(12) United States Patent
Jaffer et al.

(10) Patent No.: US 8,864,821 B2
(45) Date of Patent: Oct. 21, 2014

(54) METHODS AND COMPOSITIONS FOR IDENTIFYING SUBJECTS AT RISK OF DEVELOPING STENT THROMBOSIS

(75) Inventors: Farouc Jaffer, Jamaica Plain, MA (US); Milind Rajopadhye, Westford, MA (US)

(73) Assignee: VisEn Medical, Inc., Waltham, MA (US)

( * ) Notice: Subject to any disclaimer, the term of this patent is extended or adjusted under 35 U.S.C. 154(b) by 558 days.

(21) Appl. No.: 12/625,264

(22) Filed: Nov. 24, 2009

(65) Prior Publication Data

US 2010/0268070 A1    Oct. 21, 2010

Related U.S. Application Data

(60) Provisional application No. 61/118,099, filed on Nov. 26, 2008.

(51) Int. Cl.
| A61F 2/82 | (2013.01) |
| A61B 5/00 | (2006.01) |
| A61B 5/02 | (2006.01) |
| A61K 49/00 | (2006.01) |

(52) U.S. Cl.
CPC ........... *A61B 5/02007* (2013.01); *A61B 5/0071* (2013.01); *A61B 5/0066* (2013.01); *A61B 5/0084* (2013.01); *A61B 5/0086* (2013.01); *A61B 5/0073* (2013.01); *A61B 5/0068* (2013.01); *A61K 49/0034* (2013.01)
USPC .......... 623/2.34; 623/1.46; 600/369; 600/317; 600/322; 600/341

(58) Field of Classification Search
USPC ........... 623/1.34, 1.46; 424/9.3, 9.341, 9.351, 424/9.6, 423; 600/312, 321, 329, 369, 317, 600/322, 341
See application file for complete search history.

(56) References Cited

U.S. PATENT DOCUMENTS

| 4,981,977 | A |  | 1/1991 | Southwick et al. |
| 5,268,486 | A |  | 12/1993 | Waggoner et al. |
| 5,486,616 | A |  | 1/1996 | Waggoner et al. |
| 5,569,587 | A |  | 10/1996 | Waggoner |
| 5,569,766 | A |  | 10/1996 | Waggoner et al. |
| 5,593,658 | A |  | 1/1997 | Bogdanov et al. |
| 5,627,027 | A |  | 5/1997 | Waggoner |
| 5,632,968 | A |  | 5/1997 | Goldenberg |
| 5,808,044 | A |  | 9/1998 | Brush et al. |
| 5,843,402 | A |  | 12/1998 | Stuttle |
| 5,877,310 | A |  | 3/1999 | Reddington et al. |
| 6,002,003 | A |  | 12/1999 | Shen et al. |
| 6,004,536 | A |  | 12/1999 | Leung et al. |
| 6,008,373 | A |  | 12/1999 | Waggoner et al. |
| 6,043,025 | A |  | 3/2000 | Minden et al. |
| 6,083,481 | A |  | 7/2000 | Dean et al. |
| 6,083,485 | A |  | 7/2000 | Licha et al. |
| 6,083,486 | A |  | 7/2000 | Weissleder et al. |
| 6,121,426 | A |  | 9/2000 | Vogel et al. |
| 6,127,134 | A |  | 10/2000 | Minden et al. |
| 6,130,094 | A |  | 10/2000 | Waggoner et al. |
| 6,133,445 | A |  | 10/2000 | Waggoner et al. |
| 6,136,612 | A |  | 10/2000 | Della Ciana et al. |
| 6,210,655 | B1 |  | 4/2001 | Stein |
| 6,448,008 | B1 |  | 9/2002 | Caputo et al. |
| 6,534,041 | B1 |  | 3/2003 | Licha et al. |
| 6,592,847 | B1 |  | 7/2003 | Weissleder et al. |
| 6,690,962 | B2 |  | 2/2004 | Schmitz et al. |
| 6,740,755 | B2 |  | 5/2004 | Caputo et al. |
| 6,747,159 | B2 |  | 6/2004 | Caputo et al. |
| 7,220,401 | B2 |  | 5/2007 | Lanza et al. |
| 7,238,341 | B2 |  | 7/2007 | Zhang et al. |
| 7,947,256 | B2 | * | 5/2011 | Rajopadhye et al. .......... 424/9.6 |
| 8,029,766 | B2 | * | 10/2011 | Elmaleh et al. ................ 424/9.6 |
| 8,173,819 | B2 |  | 5/2012 | Rajopadhye et al. |
| 2003/0219383 | A1 | * | 11/2003 | Weissleder et al. ............ 424/9.6 |

(Continued)

FOREIGN PATENT DOCUMENTS

| EP | 1065250 A1 | 1/2001 |
| WO | WO-97/40104 A1 | 10/1997 |

(Continued)

OTHER PUBLICATIONS

Abd-Elgaliel et al. (2008) "Design, Synthesis and Biological Evaluation of a Radiolabelled Antagonist-Bombesin Analog as Targeting Vector," Bioconj. Chem. 19:2040-2048.
Achilefu et al. (2000) "Novel Receptor-Targeted Fluorescent Contrast Agents for In Vivo Tumor Imaging," Invest. Radiol. 35:479-485.
Addicks et al. (2002) "Synthesis and biological investigation of novel tricyclic benzodiazepinedione-based RGD analogues," ChemBioChem 3:1078-1088.
Aruva et al. (2006) "Imaging thromboembolism with fibrin-avid 99mTc-peptide: evaluation in swine," J. Nucl. Med. 47:155-162.

(Continued)

*Primary Examiner* — David Isabella
*Assistant Examiner* — Suba Ganesan
(74) *Attorney, Agent, or Firm* — Goodwin Procter LLP

(57) ABSTRACT

The invention provides methods and compositions for determining whether a subject containing a stent immobilized in a blood vessel has asymptomatic stent thrombosis or is at risk of developing clinically symptomatic stent thrombosis. In one approach, the method involves imaging a region of the blood vessel that contains the stent using a probe that contains a fluorochrome, for example, a near-infrared fluorochrome, and a targeting moiety that binds a molecular marker indicative of the presence of asymptomatic stent thrombosis or the development of symptomatic stent thrombosis. To the extent that the subject displays one or more such markers, the probe binds to the markers and increases the local concentration of the probe in the vicinity of the stent. The imaging method identifies those patients that display a higher density of such markers in the vicinity of the stent. As a result, those patients can be monitored for, and/or treated to prevent, symptomatic stent thrombosis.

6 Claims, 1 Drawing Sheet

(56) References Cited

U.S. PATENT DOCUMENTS

| 2005/0169843 | A1* | 8/2005 | Weissleder et al. ............ 424/9.6 |
| 2006/0239916 | A1 | 10/2006 | Licha et al. |
| 2009/0130024 | A1* | 5/2009 | Narayanan et al. ............ 424/9.6 |
| 2009/0220430 | A1 | 9/2009 | Rajopadhye et al. |
| 2010/0172841 | A1 | 7/2010 | Peterson et al. |
| 2011/0165075 | A1 | 7/2011 | Rajopadhye et al. |
| 2011/0171136 | A1 | 7/2011 | Poss et al. |

FOREIGN PATENT DOCUMENTS

| WO | WO-99/51702 A1 | 10/1999 |
| WO | WO-01/21624 A1 | 3/2001 |
| WO | WO-2007/136413 | 11/2007 |

OTHER PUBLICATIONS

Ballou et al. (1997) "Tumor Detection and Visualization Using Cyanine Fluorochrome-Labeled Antibodies," Biotechnol. Prog. 13:649-658.
Batt et al. (2000) "Disubstituted indazoles as potent antagonists of the integrin alpha(v)beta(3)," J. Med. Chem. 43:41-58.
Becker et al. (2001) "Receptor-Targeted Optical Imaging of Tumors with Near-Infrared Fluorescent Ligands," Nature Biotech. 19:327-331.
Blue et al. (2008) "Application of high-throughput screening to identify a novel alphaIIb-specific small-molecule inhibitor of alphaIIb-beta3-mediated platelet interaction with fibrinogen," Blood 111:1248-1256.
Bogdanov et al. (1995) "Long-circulating blood pool imaging agents," Adv. Drug Deliv. Rev. 16:335-348.
Botnar et al. (2004) "In Vivo Magnetic Resonance Imaging of Coronary Thrombosis Using a Fibrin-Binding Molecular Magnetic Resonance Contrast Agent," Circulation 110:1463-1466.
Bugaj et al. (2001) "Novel Fluorescent Contract Agents for Optical Imaging of in vivo Tumor Based on a Receptor-Target Dye-Peptide Conjugate Platform," J. Biomed. Opt. 6:122-133.
Colombo et al. (2006) "Drug-Eluting Stent Thrombosis. Increasingly Recognized But Too Frequently Overemphasized," JACC 48:203-205.
Flaumenhaft et al. (2007) "Localization and Quantification of Platelet-Rich Thrombi in Large Blood Vessels With Near-Infared Fluorescence Imaging," Circulation 115:84-93.
Hansch et al. (2004) "Diagnosis of Arthritis Using Near Infrared Fluorochrome Cy 5.5," Investigative Radiology 39(10): 626-632.
Maeshima et al. (2001) "Extracellular matrix-derived peptide binds to $\alpha_v\beta_3$ integrin and inhibits angiogenesis," J. Biol. Chem. 276(34):31959-31968.
Howie et al. (1998) "Synthetic peptides representing discontinuous CD4 binding epitopes of HIV-1 gp120 that induce T cell apoptosis and block cell death induced by gp120," The FASEB Journal 12:991-998.
Jaffer et al. (2002) "In vivo imaging of thrombin activity in experimental thrombi with thrombin-sensitive near-infrared molecular probe," Arterioscler. Thromb. Vasc. Biol. 22:1929-1935.
Jaffer et al. (2004) "Molecular imaging of factor XIIIa activity in thrombosis using a novel, near-infrared fluorescent contrast agent that covalently links to thrombi," Circulation 110:170-176.
Joner et al. (2006) "Pathology of Drug-Eluting Stents in Humans. Delayed Healing and Late Thrombotic Risk," JACC 48:193-202.
Kelly et al. (2005) "Detection of vascular adhesion molecule-1 expression using a novel multimodal nanoparticle," Circ. Res. 96:327-336.
Kim et al. (2003) "Type-II Quantum Dots: CdTe/CdSe(Core/Shell) and CdSe/ZnTe(Core/Shell) Heterostructures," J. Am. Chem. Soc. 125: 11466-11467.
McCarthy et al. (2009) "Multimodal Nanoagents for the Detection of Intravascular Thrombi," Bioconjugate Chem. 20:1251-1255.
McGrath et al. (2003) "Peptide ketobenzoxazole inhibitors bound to cathepsin K," Biochemistry 42(51):15018-28.
Montet et al. (2006) "Nanoparticle imaging of integrins on tumor cells," Neoplasia 8:214-222.
Nahrendorf et al. (2006) "Noninvasive vascular cell adhesion molecule-1 imaging identifies inflammatory activation of cells in atherosclerosis," Circulation 114:1504-1511.
Nakazawa et al. (2007) "The Significance of Preclinical Evaluation of Sirolimus-, Paclitaxel-, and Zotarolimus-Eluting Stents," The American Journal of Cardiology 100:36M-44M.
Neri et al. (1997) "Targeting by Affinity-Matured Recombinant Antibody Fragments of an Angiogenesis Associated Fibronectin Isoform," Nature Biotech. 15:1271-1275.
O'Neil et al. (1992) "Identification of novel peptide antagonists for GPIIb/IIIa from a conformationally constrained phage peptide library," Proteins 14(4):509-515.
Ozmen, et al. (2000) "Infrared fluorescence sensing of submicromolar calcium: pushing the limits of photoinduced electron transfer," Tetrahedron Letters 41 p. 9185-9188.
Pislaru et al. (2006) "Magnetically targeted endothelial cell localization in stented vessels," J. Am. Coll. Cardiol. 48(9):1839-45.
Raboisson et al. (2007) "Identification of novel short chain 4-substituted indoles as potent alphavbeta3 antagonist using structure-based drug design," Eur. J. Medicinal Chemistry 42:334-343.
Sendzik et al. (2005) "Fluoroquinolones cause changes in extracellular matrix, signalling proteins, metalloproteinases and caspase-3 in cultured human tendon cells," Toxicology 212:24-36.
Sosnovik et al. (2005) "Magnetic resonance imaging of cardiomyocyte apoptosis with a novel magneto-optical nanoparticle," Magn. Reson. Med. 54:718-724.
Tung et al. (2003) "Novel factor XIII probes for blood coagulation imaging," ChemBioChem 4:897-899.
Yang et al. (2005) "Discovery of Small-Molecule Human Immunodeficiency Virus Type 1 Entry Inhibitors That Target the gp120-Binding Domain of CD4*," Journal of Virology, p. 6122-6133.

* cited by examiner

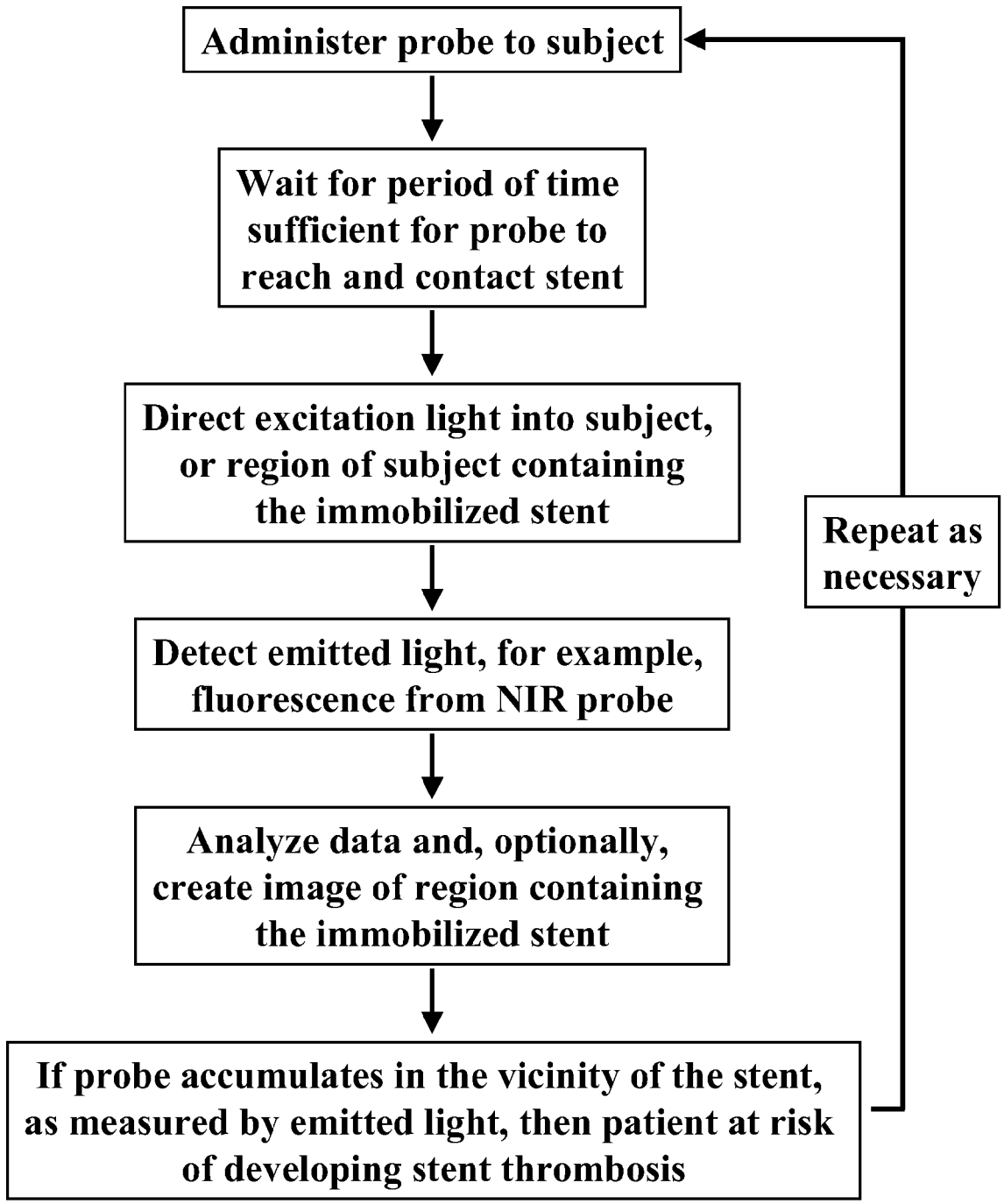

METHODS AND COMPOSITIONS FOR IDENTIFYING SUBJECTS AT RISK OF DEVELOPING STENT THROMBOSIS

CROSS-REFERENCE TO RELATED APPLICATIONS

This application claims the benefit of and priority to U.S. Provisional Patent Application No. 61/118,099, filed Nov. 26, 2008, the entire contents of which are incorporated by reference herein.

FIELD OF THE INVENTION

The invention relates generally to methods and compositions for identifying a subject at risk of developing stent thrombosis, and, more particularly, the invention relates to in vivo imaging methods and compositions for identifying a subject at risk of developing stent thrombosis.

BACKGROUND

Complications associated with atherosclerotic vascular disease including heart attacks, stroke, and ischemic limbs are major medical problems. The implantation of intravascular stents, including drug-eluting stents and bare metal stents, to maintain the patency of blood vessels has become the standard of care for the treatment of a number of disorders including, for example, symptomatic coronary artery disease, cerebrovascular disease, and peripheral arterial disease.

Coronary stent implantation currently is a $6 billion business, with Americans receiving an estimated 1.5 million stents per year. One issue associated with the use of bare metal stents is the incidence of restenosis (scar tissue formation), which is the recurrence of narrowing of the blood vessel following stent implantation. A variety of drug-eluting stents have been developed to address this issue, and polymer-based sirolimus-eluting stents (Cypher, Cordis Corp., Miami Lakes, Fla.) and paclitaxel-eluting stents (Taxus, Boston Scientific Corp., Natick, Mass.) and zotarolimus-eluting stents (Endeavor, Medtronic) and everolimus-eluting stents (Xience, Abbott Vascular) have been approved for human use in the United States of America. Since their introduction several years ago, drug-eluting stents have captured approximately 70-80% percent of the U.S. stent market, due mainly to their ability to prevent or reduce the incidence of restenosis.

Recently, the enthusiasm of drug eluting stents has been dampened by safety concerns associated with an increased risk of stent thrombosis occurring more than 30 days after implantation (termed late stent thrombosis). It appears that late stent thrombosis occurs more frequently following implantation of drug eluting stents relative to bare metal stents. (See, Nakazawa et al. (2007) AM. J. CARDIOL. 100: 36M-44M; Joner et al. (2006) J. AM. COLL. CARDIO. 48:193-202.) The emergence of late stent thrombosis, i.e., thrombosis occurring more than 30 days after implantation, resulting from the use of drug-eluting stents is causing medical, legal, and financial concerns for clinicians, patients, stent companies, and regulatory authorities. The problem of stent thrombosis is likely to persist indefinitely with the current generation of drug eluting stents, as stent thrombosis occurs steadily at a rate of 0.4-0.6% per year (Wenaweser et al. (2008) J. AM. COLL. CARDIO. 52:1134-1140).

Due to the association between late stent thrombosis and high morbidity rates, there exists a need for approaches that permit the identification of subjects at risk of developing stent thrombosis well before the onset of clinically-apparent symptoms, which, once identified, may be too late to treat the subject due to a high rates of myocardial infarction and death (Iakovou (2005) JAMA 293:2126-2130). Once subjects at risk of developing stent thrombosis have been identified they can be monitored more regularly and/or provided with or maintained on preventative or prolonged therapies, for example, anti-platelet or anti-coagulant therapies, so as to reduce the risk of stent thrombosis. Furthermore, there is an ongoing need to be able to evaluate the effectiveness of new anti-stent thrombosis therapies and therapeutic approaches (including but not limited to new stents, balloon catheters, drugs, or cells/biological therapies) in vivo in preclinical animal models, during clinical trials and in patients.

SUMMARY OF THE INVENTION

The invention is based, in part, upon the discovery that an in vivo molecular imaging method can be used to identify subjects, which contain an implanted stent, for example, drug-eluting or bare metal stent, that are at risk of developing symptomatic stent thrombosis. Those subjects, once identified, can be monitored for the development of symptomatic stent thrombosis and/or treated with one or more agents, for example, anticoagulants, to prevent, slow down or stop the formation of stent thrombosis or to reverse existing asymptomatic stent thrombosis. As used herein, the term "asymptomatic stent thrombosis" is understood to mean a condition when microscopic thrombi, for example, thrombi less than about 100 micrometers in diameter, are present in the vicinity of the stent but where there are no clinical symptoms of occlusion or blood clot formation. In contrast, "symptomatic stent thrombosis" is understood to mean a condition where clinical symptoms of occlusion or blood clot formation have developed, which include, for example, impeded blood flow in a blood vessel, delayed healing (characterized by, for example, endothelialization at the site of the stent), heart attack or death.

In one aspect, the invention provides an in vivo molecular imaging method for determining whether a subject (for example, a mammal, for example, a human) containing a stent immobilized in a blood vessel of the subject has asymptomatic stent thrombosis or is at risk of developing future stent thrombosis. The method comprises the steps of: (a) administering to the subject an imaging probe, for example, a molecular or cellular imaging probe, comprising a targeting moiety that binds a molecular marker indicative of the development of stent thrombosis associated with a fluorescence imaging moiety, for example, a fluorochrome (for example, a near-infrared fluorochrome); (b) directing excitation light, for example, near-infrared light, into a region of the subject containing the stent; and (c) detecting fluorescent light emitted from the region thereby to determine whether the subject is at risk of developing stent thrombosis. In addition to high sensitivity and multichannel capabilities, a major advantage of fluorescence, as an exemplary molecular imaging modality, is the availability of clinically translatable fluorescence catheter systems that can detect fluorochromes in coronary-sized vessels (Jaffer et al. (2008) CIRCULATION 118:1802-1809).

The fluorescent light emitted from the subject can be processed to create an image representation, for example, a reflectance or tomographic image, of at least the region containing the immobilized stent. The representation can then be co-registered with an image representation of at least the region obtained by X-ray, magnetic resonance, computed tomography, ultrasound, single photon emission tomography, positron emission tomography, optical coherence tomography/optical frequency domain imaging, near infrared spectroscopy, or other imaging/sensing modality.

It is understood that the molecular marker bound by the probe can be any molecular marker indicative of the development of stent thrombosis and can include a cellular marker. In general, molecular markers include components indicative of inflammation (for example, increased numbers of immune cells and/or increased numbers of activated immune cells) and blood clot formation (for example, fibrin or platelet deposition) at the site of the stent. It is contemplated that a plurality of different probes can be used simultaneously (for example through multi-wavelength fluorescence imaging) to interrogate whether a number of different molecular markers are present or present at elevated levels in the vicinity if the stent.

Exemplary biochemical and cellular markers for stent thrombosis include, for example, components of the blood coagulation cascade (for example, activated Factor VIII, activated Factor X, activated Factor V, thrombin (activated Factor II), fibrin (activated Factor I), and activated Factor XIIIa, integrins, bombesin, CD4, VCAM-1, cells (for example, activated, dysfunctional, or abnormal endothelial cells, immune cells (for example, macrophages, lymphocytes, eosinophils, giant cells, and neutrophils) and smooth muscle cells), cell receptors (for example, immune receptors, growth factor receptors, cytokine receptors), and proteases (for example, cathepsins, cysteine proteases, matrix metalloproteinases, glutamic acid proteases, threonine proteases, serine proteases, and aspartic proteases).

The probe comprises one or more fluorescence imaging moieties, for example, fluorochromes or fluorescent particles attached, for example, covalently or non-covalently attached, to a targeting moiety that binds preferentially to a molecular marker indicative of stent thrombosis.

The targeting moiety can be, for example, a cell, liposome, a macromolecule (for example, a protein (for example, an antibody), peptide, carbohydrate, lipid, glycoprotein, glycolipid, nucleic acid (for example, an aptamer), or a small molecule. The fluorescence imaging moieties can be covalently associated with the cell or liposome (for example, covalently linked to a subcellular component or macromolecule disposed within or upon an outer surface of the cell or liposome), or non-covalently associated with (for example, encapsulated within) the cell or liposome. Alternatively, in the case of a macromolecule or small molecule, the fluorescence moiety can be covalently or non-covalently associated with the macromolecule or small molecule. To the extent that the fluorescence moiety is covalently associated with the targeting moiety, the fluorescence moiety can be linked directly or indirectly (for example, via a linker or carrier) to the targeting moiety. It is understood that probe can comprise a single or a plurality of fluorescence moieties and/or a single or a plurality of targeting moieties.

It is understood that a variety of different fluorescence imaging moieties (for example, fluorochromes or fluorescent particles) can be used to make probes useful in the practice of the invention. Preferred fluorochromes include near-infrared fluorochromes (NIRF), where the near-infrared fluorochromes can be a carbocyanine fluorochrome, for example, an indocarbocyanine fluorochrome. Exemplary near-infrared fluorochromes can be selected from the group consisting of Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, and DyLight647, HiLyte Fluor 680, HiLyte Fluor 750, IRDye800CW, IRDye 800RS, IRDDye 700DX, ADS780WS, and ADS832WS.

In certain embodiments, the imaging probe further comprises (i) a fluorochrome attachment moiety comprising a fluorescence activation site (for example, a protease cleavage site) and (ii) a second near-infrared fluorochrome. The first and second near-infrared fluorochromes are covalently linked to the fluorochrome attachment moiety at fluorescence-quenching interaction-permissive sites, and the imaging probe is activated by cleavage at the fluorescence activation site. Exemplary fluorescence activation sites include a protease cleavage site for one or more protease enzymes selected from the group consisting of cathepsin (for example, cathepsin B/H, cathepsin D), metalloproteinase (for example, gelatinases MMP-2 and MMP-9), a serine protease (for example, thrombin, see Jaffer et al. (2002) ARTERIOSCLEROSIS THROMBOSIS VASCULAR BIOLOGY 22:1929-1935), an aspartic protease, cysteine protease, threonine protease and glutamic acid protease.

In certain embodiments, the delivery of the excitation light and/or the detection of the emitted fluorescent light can be facilitated by one or more of an endoscope/angioscope, catheter, planar system, reflectance system, tomographic system, confocal system, laser scanning system, optical imaging system and/or an intraoperative microscope. Furthermore, depending upon the probe and detection method chosen, the blood vessel optionally contains blood traversing the stent. In certain approaches, however, the blood vessel is locally occluded and does not permit blood to pass therethrough. Alternatively, and in certain circumstances, the blood passing through the vessel may have been replaced with a saline or a blood substitute, for example, perfluorocarbon, such as, perflubron.

In another aspect, the invention provides a stent capable of being imaged in vivo. The stent comprises (a) a stent dimensioned for implantation within a blood vessel; (b) a coating covering at least a portion of the stent; and (c) an activatable imaging probe or a targeted imaging probe, each of which can be associated with either the coating or a surface, for example, a metal surface, of the stent. The activatable imaging probe comprises a fluorochrome attachment moiety and a plurality of near-infrared fluorochromes linked to the fluorochrome attachment moiety at fluorescence-quenching interaction-permissive positions. The fluorescence-quenching interaction-permissive positions are separated by a fluorescence activation site (for example, a protease cleavage site), wherein in the intact probe a first near-infrared fluorochrome quenches a second near-infrared fluorochrome. The probe is activatable by cleavage at the fluorescence activation site whereupon the first fluorochrome no longer quenches the second fluorochrome. Depending upon the choice of the fluorescence activation site, the probe can be activated when exposed to a molecular marker indicative of stent thrombosis. In the case of an activatable probe, the implanted stents cannot be visualized until the surrounding environment activates the probe. In the case of targeted probes, the intensity and duration of signal is related to the presence of the molecular target.

These and other aspects and features of the invention are described in the following detailed description and claims.

BRIEF DESCRIPTION OF THE DRAWINGS

The invention is illustrated but is not limited by the annexed drawing, in which:

FIG. 1 is a flow chart showing a protocol for determining whether a subject is at risk of developing stent thrombosis.

DETAILED DESCRIPTION

The invention is based, in part, upon the discovery that an in vivo molecular imaging method can be used to identify a subject, which contains an immobilized stent that is at risk of developing clinically symptomatic stent thrombosis. Those subjects, once identified, can be monitored for the development of asymptomatic or symptomatic stent thrombosis and/or treated with one or more agents, for example, anticoagulants or anti-platelet agents, to prevent, slow down or stop the formation of stent thrombosis or to reverse the development of stent thrombosis. The invention is particularly useful when a drug-eluting stent, for example, a stent that releases a drug, for example, paclitaxel (a paclitaxel-eluting stent), sirolimus (a sirolimus-eluting stent), or zotarolimus (a zotarolimus-eluting stent), or everolimus (an everolimus-eluting stent) has been implanted in or immobilized within a blood vessel of the subject.

In one aspect, the invention provides an in vivo molecular imaging method for determining whether a subject containing a stent immobilized in a blood vessel of the subject is at risk of developing stent thrombosis. The method comprises the steps of: (a) administering to the subject an imaging probe comprising a targeting moiety that binds a molecular marker indicative of the development of stent thrombosis associated with a fluorescence imaging moiety, for example, a fluorochrome, for example, a near-infrared fluorochrome; (b) directing excitation light, for example, near-infrared light, into a region of the subject containing the stent; and (c) detecting fluorescent light emitted from the region so as to determine whether the subject is at risk of developing stent thrombosis.

The fluorescent light emitted from the subject can be processed to create an image representation, for example, a reflectance or a tomographic image representation, of at least the region containing the stent. The term, "image representation," as used herein is understood to mean a visual display or any data representation that may be interpreted for visual display. The image representation can then be co-registered with an image of at least the region obtained by X-ray, magnetic resonance, computed tomography, ultrasound, single photon emission tomography, spectroscopy, optical coherence tomography/optical frequency domain imaging, near infrared spectroscopy, positron emission tomography, or other imaging/sensing modality.

I. Probe Considerations

It is understood that a variety of different types of imaging probes can be used in the methods of the present invention and include (1) probes that become activated after target contact (e.g., binding or interaction) (Weissleder et al. (1999) NATURE BIOTECH. 17:375-378; Bremer et al. (2001) NATURE MED. 7:743-748; Meade, Conti et al. (2003) NUCLEAR MEDICINE AND BIOLOGY 30:261-265; Jaffer et al (2007) CIRCULATION 116:1052-1061; Jaffer et al. (2008) CIRCULATION 118:1802-1809), (2) wavelength shifting beacons (Tyagi et al. (2000) NATURE BIOTECHNOL. 18:1191-1196), (3) multicolor fluorescence probes (Tyagi et al. (1998) NATURE BIOTECHNOL. 16:49-53), (4) probes that have high binding affinity to targets, i.e., that remain within a target region while non-specific probes are cleared from the body (Achilefu et al. (2000) INVEST. RADIOL. 35:479-485; Becker et al. (2001) NATURE BIOTECH. 19:327-331; Bujai et al. (2001) J. BIOMED. OPT. 6:122-133; Ballou et al. (1997) BIOTECHNOL. PROG. 13:649-658; and Neri et al. (1997) NATURE BIOTECH. 15:1271-1275), and (5) fluorescent semiconductor based probes (i.e., Quantum Dots Bawendi et al. (2003) J. AM. CHEM. SOC. 125: 11466-11467).

Probes useful in the practice of the invention generally are water soluble or water dispersible (i.e., are sufficiently soluble or suspendable in aqueous or physiological media solutions). The in vivo half-life of the agent can be designed to be at least about 10 minutes, but more preferably 30 minutes to several hours. The in vivo half-life of the agent preferably is a time (for example, at least about 30 minutes) sufficient to achieve exposure and binding to a region surrounding the implanted stent. In certain embodiments, the probe is water soluble or dispersible in aqueous media, and is biocompatible i.e., non-toxic having, for example, an $LD_{50}$ of greater than about 50 mg/kg body weight. The agents also preferably do not have any undesired phototoxic properties and/or display low serum protein binding affinity.

The various features of the probes, namely, the targeting moiety, the fluorescence moiety, and, where applicable, carrier are discussed in the following sections.

A. Targeting Moiety

The probe comprises one or more fluorescence imaging moieties associated, for example, covalently associated or non-covalently associated, with a targeting moiety, which can be, for example, a cell, liposome, a macromolecule (for example, a protein (for example, an antibody), a peptide, a carbohydrate, a lipid, a glycoprotein, a glycolipid, or a nucleic acid (for example, an aptamer)), or a small molecule.

The fluorescence imaging moiety can be covalently associated with the cell or liposome (for example, covalently linked to a subcellular component or macromolecule disposed within or upon an outer surface of the cell or liposome), or non-covalently associated with (for example, encapsulated within) the cell or liposome. Alternatively, in the case of the macromolecule or small molecule, the fluorescence imaging moiety can be covalently or non-covalently associated with the macromolecule or small molecule.

The targeting moiety binds preferentially to a biological marker indicative of the future development of clinically symptomatic stent thrombosis. It is understood that exemplary markers of stent thrombosis include components indicative of an inflammatory response (for example, increased numbers of immune cells and/or increased numbers of activated immune cells). Exemplary immune cells include macrophages, lymphocytes, eosinophils, giant cells, and neutrophils. Other exemplary markers include components indicative of blood clot formation including, for example, one or more members of the intrinsic clotting pathway (for example, Activated Factor VII), and/or one or more members of the extrinsic clotting pathway (for example, activated Factor XII, activated Factor XI, activated Factor IX, activated Factor VIII, and/or one or more members of the clotting cascade common to both the intrinsic pathway and the extrinsic pathway (for example, activated Factor X, activated Factor V, thrombin (activated Factor II), fibrin (activated Factor I), and activated Factor XIIIa).

Other markers include partial epithelialization of the stent in the blood vessel. Exemplary cells that can be imaged to provide an assessment of whether epithelialization of the stent has been partial or complete include endothelial cells (including markers associated with the endothelial cells, such as, platelet endothelial cell adhesion molecule (PECAM-1), thrombomodulin, vascular adhesion molecule (VCAM-1), fibronectin, and intercellular adhesion molecule (ICAM-1), and smooth muscle cells (including markers associated with the muscle cells, such as, extracellular matrix proteins, adherens junction proteins, caveolae, gap junction proteins. In addition, other markers include proteases (for example, cathepsin, matrix metalloproteinases, cysteine protease, serine proteases, and aspartic proteases).

It is understood that the targeting moiety can be a cell or liposome that binds preferentially to the molecular marker in vivo. Binding can be facilitated, for example, through a binding moiety (for example, receptor, ligand, antibody) immobilized within or upon the outer membrane of the cell or liposome. Alternatively, the targeting moiety can be a macromolecule, for example, protein, peptide, nucleic acid, carbohydrate, lipid, glycoprotein, or a glycolipid. Exemplary macromolecules include, for example, antibodies or antigen binding fragments thereof, biosynthetic antibody binding sites, ligands for cell receptors, cell receptors, enzyme substrates, enzyme cofactors, biotin, hormones, neurotransmitters, growth factors, cytokines, lymphokines, lectins, integrins, selectins, and toxins. Certain targeting moieties useful in the practice of the invention bind to one or more of the following molecular markers: a VEGF receptor, PDGF receptor, HER2, SSKI, EphB4, EGFR, FGFR, VEGFR-2, VEGFR-3, serine/threonine and receptor kinases, FLT-3, type III RTKs, c-KIT, Bcr-Abl, CSF-1R, CCR-2, RET, VDGF-2, ICAM-1, PECAM-1, and VCAM-1.

Furthermore, exemplary targeting moieties include, for example, small molecules, for example, argatroban that binds thrombin; hirudin that binds thrombin, tetraiodothyroacetic acid that binds the integrin receptor, tyrosine kinase inhibitors that bind VEGF receptor, panitumumab that binds EGF receptor, cetuximab that binds EGF receptor, and lapatinib that binds HER2.

In one embodiment, the targeting moiety is an antibody, for example, a monoclonal antibody, an antigen binding fragment of an antibody, or a biosynthetic antibody binding site. Antibody fragments include Fab, Fab', (Fab')$_2$ or Fv fragments. The antibodies and antibody fragments can be produced using conventional techniques known in the art. A number of biosynthetic antibody binding sites are known in the art and include, for example, single chain Fv or sFv molecules, described, for example, in U.S. Pat. Nos. 5,091,513, 5,132,405, and 5,476,786. Other biosynthetic antibody binding sites include bispecific or bifunctional binding proteins, for example, bispecific or bifunctional antibodies, which are antibodies or antibody fragments that bind at least two different antigens. Methods for making bispecific antibodies are known in art and, include, for example, by fusing hybridomas or by linking Fab' fragments. See, e.g., Songsivilai et al. (1990) CLIN. EXP. IMMUNOL. 79: 315-325; Kostelny et al. (1992) J. IMMUNOL. 148: 1547-1553.

Antibodies that bind molecular markers for stent thrombosis are available commercially. Anti-thrombin antibodies (for example, ab48626, ab30973 and ab61367) are available commercially from AbCam (Cambridge, Mass.). Anti-fibrin alpha chain antibodies (for example, ab19079 Fibrin alpha chain antibody [UC45]) are available commercially from AbCam. Anti-CD4 antibodies (for example ab846 CD4 antibody [BC/1F6]) are available commercially from AbCam. Anti-integrin antibodies (for example, ab52971 Integrin beta 1 antibody [EP1041Y]-Carboxyterminal end and ab7167 Integrin beta 3 antibody [BV4]) are available commercially from AbCam. Anti-VCAM-1 antibodies (for example ab19264 VCAM1 [1.G1b1] antibody and ab7219 VCAM1 antibody [1G11B1]), are available commercially from AbCam. Anti-HER2, also known as ErbB 2, antibodies (for example, ab2428 ErbB 2 antibody and ab16901 ErbB 2 antibody [3B5]) are available commercially from AbCam. Anti-EphB4 antibodies (for example, ab66336 Eph receptor B4 antibody [4A12G8.5G2F8] and ab70404 Eph receptor B4 antibody [7H4A6]) are available commercially from AbCam. Anti-EGFR antibodies (for example, ab2430 EGFR antibody and ab62 EGFR antibody [F4]) are available commercially from AbCam. Anti-FGFR antibodies (for example, ab10646 FGFR1 antibody, ab10648 FGFR2 antibody, ab10649 FGFR3 antibody, and ab41948 FGFR4 antibody) are available commercially from AbCam. Anti-VEGFR-2 antibodies (for example, ab9530 VEGF Receptor 2 antibody [KDR/EIC] and ab10972 VEGF Receptor 2 antibody) are available commercially from AbCam. Anti-FLT-3 (also known as FLK-2 and CD135) antibodies (for example, Flt3 ligand antibody [EP1140Y], ab37847 Flt3/CD135 antibody—Aminoterminal end) are available commercially from AbCam. Anti-CCR-2 antibodies (for example, ab1668 CCR2 antibody and ab13310 CCR2 antibody) are available commercially from AbCam. Anti-RET antibodies (for example, ab1840 Ret antibody [RET01] and ab51122 Ret antibody) are available commercially from AbCam. In addition, anti-Bcr-Abl antibodies (for example, BCR-ABL monoclonal antibody (clone 4C12)) are available from Cancer Research Technology (CRT, London, UK). Antibodies against type III RTKs are also available commercially, and include anti-VEGFR-1 antibodies, (for example, ab32152 VEGF Receptor 1 antibody [Y103] and ab2350 VEGF Receptor 1 antibody, available from AbCam), anti-PDGFR-β antibodies, (for example, ab10847 PDGF Receptor beta antibody [PDGFR-B2] and ab32570 PDGF Receptor beta antibody [Y92], available from AbCam), anti-PDGFR-α antibodies (for example, ab61219 PDGF Receptor alpha antibody and ab62620 PDGF Receptor antibody, available from AbCam), anti-CSF-1R (also known as MCSF Receptor) antibodies (for example, ab32633 MCSF Receptor antibody and ab37858 MCSF Receptor antibody, available from AbCam), anti-c-KIT antibodies (for example, 16832 anti-c-Kit antibody, available from AbCam), anti-VEGFR-3 (also known as FLT-4) antibodies (for example, ab27278 VEGF Receptor 3 antibody and ab10284 VEGF Receptor 3 antibody, available from AbCam). Anti-ICAM1 antibodies (for example, ab20 ICAM1 antibody [15.2] and ab19756 ICAM1 antibody [15.2]) are available commercially from AbCam. Anti-PECAM1 antibodies (for example, anti-PECAM1 antibody [P8590] and monoclonal anti-CD31 (PE-CAM-1) antibody) are available commercially from Sigma Aldrich.

Antibodies that bind epithelial cells are available commercially. For example, the anti-cytokeratin antibodies (for example, MAB1636, MAB3412, MAB3224, MAB1603, and MAB1631) that bind cytokeratin on the surface of epithelial cells are available commercially from Millipore.

Peptides that bind molecule markers targets for stent thrombosis are available commercially or can be synthesized using routine peptide synthesis chemistries. Peptides that preferentially bind thrombin include Gln-Leu-Trp-Gly-Ser-His (SEQ ID NO.:1), Arg-Gln-Leu -Trp-Gly-Ser-His (SEQ ID NO.:2), His-Gln-Leu-Trp-Gly-Ser-His (SEQ ID NO.:3), and Tyr-Phe-Pro-Gly-Pro -Tyr-Leu (SEQ ID NO.:4) (as disclosed in U.S. Pat. No. 5,831,003). Peptides that preferentially bind fibrin include Asp-Asp-Ala-Tyr-Leu-Asp-Asn-Glu-Lys-Glu-Arg-Glu-Glu-Tyr-Val-Leu-Asn-Asp-Ile-Gly-Val-Ile-Phe-Tyr-Gly-Glu-Asn-Val-Asn-Asp-Ile-Lys-Thr-Arg-Ser-Trp-Ser-Tyr-Gly-Gln-Phe (SEQ ID NO.:5), Asn-Lys-Leu-Ile-Val-Arg-Arg-Gly-Gln-Ser-Phe-Tyr-Val-Gln-Ile-Asp-Phe-Ser-Arg-Pro-Tyr-Asp-Pro-Arg-Arg-Asp (SEQ ID NO.:6), and Gly-Pro-Arg-Pro-Pro-Lys (SEQ ID NO.:7).

Peptides that preferentially bind integrins (for example, integrins $\alpha_{v\beta3}$ and $GP\alpha_{IIb}\beta_3$) include integrin $\alpha_v\beta_3$-binding peptides derived from tumstatin (peptides T1-T8, as disclosed in Maeshima et al. (2001) J. BIOL. CHEM. 276(34): 31959-31968) or cyclo(Arg-Gly-Asp-D-Phe-Lys) (SEQ ID NO.:8); and the cyclic, disulfide bonded forms of Arg-Gly-Asp or Lys-Gly-Asp, which bind to $GP\alpha_{IIb}\beta_3$ (O'Neil et al. (2004) PROTEINS: STRUCTURE, FUNCTION, AND BIOINFORMATICS 14(4):509-515).

Peptides that preferentially act as bombesin analogues for targeting gastrin releasing peptide receptors include Phe-Gln-Trp-Ala-Val-Gly-His-Leu (SEQ ID NO.:9) (used in Demobesin-1 and Bomproamide), Gln-Trp-Ala-Val-Gly-His-Leu (SEQ ID NO.:10) and Ser-Ser-Ser-Gln-Trp-Ala-Val-Gly-His-Leu-Met (SEQ ID NO.:11) as described in Abd-Elgaliel et al. (2008) BIOCONJ. CHEM. 19:2040-2048.

Peptides that preferentially bind CD4 include peptides 3.7, GC1, and 3.5, derived from discontinuous segments of gp120, as disclosed in Howie et al. (1998) THE FASEB JOURNAL 12:991-998. Peptides that preferentially bind VCAM-1 include Val-His-Pro-Lys -Gln-His-Arg (SEQ ID NO.:12), Val-His-Ser-Pro-Asn-Lys-Lys (SEQ ID NO.:13), Asp-His-Ala-Ser-Pro -Met-His (SEQ ID NO.:14), Pro-Thr-Arg-Ile-Glu-Gln-Met-Cys (SEQ ID NO.:15), Met-His-Arg-Ala-His-Gln-Met-Cys (SEQ ID NO.:16), and Ile-Ser-His-Gln-Met-Pro-Ala (SEQ ID NO.:17), as disclosed in Kelly et al. (2005) CIRCULATION RESEARCH 96:327-336. Peptides that preferentially bind Hepsin include Ile-Pro-Leu-Val-Leu-Pro-Leu (SEQ ID NO.:18) and Gly-Gly-Tyr-Leu-Pro-Phe-Arg-Asp-Pro-Asn-Ser-Glu-Glu-Asn-Ser-Asn-Asp-Ile-Ala-Leu (SEQ ID NO.:19), which is available commercially from Cayman Chemical Company (Ann Arbor, Mich.). Peptides that preferentially bind SPARC include, for example, Ser-Pro-Pro-Thr-Gly-Ile-Asn (SEQ ID NO.:20). Peptides that preferentially bind Cathepsin K include Val-His-Pro-Lys-Gln-His-Arg (SEQ ID NO.:21) and the peptide alpha-ketoheterocyclic inhibitors identified in McGrath et al. (2003) BIOCHEMISTRY 42(51):15018-28. Peptides that preferentially bind E-selectin include Cys-Asp-Ser-Asp-Ser-Asp-Ile-Thr-Trp-Asp-Gln-Leu-Trp-Asp-Asp-Leu-Met-Lys (SEQ ID NO.:22) and Asp-Ile-Thr-Trp-Asp-Gln-Leu-Trp-Asp-Leu-Met-Lys (SEQ ID NO.:23). Peptides that preferentially bind Tat include Arg-Arg-Arg-Arg-Gly-Arg-Arg-Arg-Arg (SEQ ID NO.:24).

Small molecules that bind molecule marker targets for stent thrombosis are available commercially or can be synthesized using synthetic chemistries. Small molecules that preferentially bind thrombin include D-Phe-Pro-Arg or D-Phe-Pro-boroArg. Small molecules that bind integrin $\alpha_v\beta_3$ include, for example, quinolone derivatives (for example fluoroquinolone and ofloxacin as disclosed in Sendzik et al. (2005) TOXICOLOGY 212:24-36), tetrahydronaphthyridine derivatives (for example, 3-(3-pyridyl)-3-[4-[2-(5,6,7,8-tetrahydro[1,8]naphthyridin-2-yl)ethyl]indol-1-yl]propionic acid 21 as disclosed in Raboisson et al. (2007) EUR. J. MEDICINAL CHEMISTRY 42:334-343), indazole derivatives (for example, Compound 34a (SM256) as disclosed in Batt et al. (2000) J. MEDICINAL CHEMISTRY 43:41-58), and benzodiazepine derivatives (for example, RGC Compounds 7 and ent-7 as disclosed in Addicks et al. (2002) CHEMBIOCHEM 3:1078-1088). Small molecules that bind integrin $GP\alpha_{IIb}\beta_3$ include, for example, Compound 1 as disclosed in Blue et al. (2007) BLOOD 111:1248-1256). Small molecules that bind CD4 include, for example, NSC 13778, as disclosed in Yang et al. (2005) J. VIROLOGY 79:6122-6133.

In general, the fluorescence imaging moieties are attached to the targeting moiety so as not to alter the activity of the targeting moiety. In certain embodiments, the targeting moieties themselves are bivalent, or multivalent, i.e., have two or more target binding sites.

In one embodiment, the probe comprises at least one thrombin targeting moiety (TTM), for example, a substituted or an unsubstituted tetrahydronaphthyridine moiety, and a fluorescence imaging moiety (F), for example, a fluorochrome, wherein one or more molecules of the TTM is chemically linked to one or more molecules of the F. In certain embodiments, the probe is a molecule having Formula I:

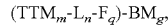
$$(TTM_m-L_n-F_q)-BM_g, \quad I$$

wherein m=1-500, n=0-500, q=1-500, and g=0-500, L is linker or bond, BM is a biocompatible molecule, for example, polyethylene glycol, dextran, and polyvinylpyrollidone, that modifies pharmacokinetics of the probe (for example, extends the circulating half life of a probe) relative to a probe lacking such a biocompatible molecule. Exemplary biocompatible molecules are also referred to herein as carriers, which are described in more detail hereinbelow in Section C.

B. Fluorescence Imaging Moiety

It is understood that probes can contain a variety of different fluorescent moieties or fluorophores, which can include, for example, a fluorochrome, a fluorochrome attached to a carrier (for example, a polymeric backbone or a particle (for example, a nanoparticle)), a fluorescent particle, and a fluorescent particle attached to a carrier (for example, a polymeric backbone or a particle), and an organometallic compound or metal complexed to a chelator.

The term, "fluorochrome," as used herein includes, but is not limited to, a fluorochrome, a fluorophore, a fluorochrome quencher molecule, a quantum dot, any organic or inorganic dye, metal chelate, or any fluorescent enzyme substrate, including, for example, a protease activatable enzyme substrate.

It is understood that a variety of fluorescent moieties can be used in the practice of the invention. The fluorescence imaging moiety can comprise fluorochromes with excitation and emission maxima in the range from about 400 nm to about 850 nm. Exemplary fluorochromes include, for example, far red and a near-infrared fluorochromes. The term "far red fluorochrome" is understood to mean any agent that has excitation and/or emission maxima from about 700 nm to about 800 nm, optionally from about 700 nm to about 760 nm. The term "near-infrared fluorochrome" is understood to mean any agent that has excitation and/or emission maxima from about 600 nm to about 1,200 nm, optionally from about 650 nm to about 850 nm.

Exemplary far red fluorochromes include Cellvue Claret, commercially available from PTI Research Inc; mKate (TagFP635), commercially available from evrogen; Katushka (TurboFP635), commercially available from evrogen; and HcRed, commercially available from evrogen.

The near-infrared fluorochromes preferably have an extinction coefficient of at least 50,000 $M^{-1}cm^{-1}$ per fluorochrome molecule in aqueous medium. The near-infrared fluorochromes preferably also have (1) high quantum yield (i.e., quantum yield greater than 5% in aqueous medium), (2) narrow excitation/emission spectrum, spectrally separated absorption and excitation spectra (i.e., excitation and emission maxima separated by at least 15 nm), (3) high chemical and photostability, (4) nontoxicity, (5) good biocompatibility, biodegradabiliy and excretability, and (6) commercial viability and scalable production for large quantities (i.e., gram and kilogram quantities) required for in vivo and human use.

Exemplary near-infrared fluorochromes include carbocyanine dyes (for example, indocarbocyanine dyes) and polymethine fluorescent dyes. A variety of different carbocyanine and polymethine fluorescent dyes can be used in the practice of the invention and include, for example, those described in U.S. Pat. Nos. 6,747,159; 6,448,008; 6,136,612; 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; also WO 97/40104, WO 99/51702, WO 01/21624, and EP 1 065 250 A1; and TETRAHEDRON LETTERS 41:9185-88 (2000). Other exemplary near-infrared fluorochromes include phthalocyanines, conjugated thiophenes, benzophenoxazines, and porphyrins.

Various near-infrared fluorochromes useful in producing the imaging probes are commercially available and include: Cy5.5, Cy5 and Cy7 (GE Healthcare); AlexaFlour660, AlexaFlour680, AlexaFluor750, and AlexaFluor790 (Invitrogen); VivoTag680, VivoTag-5680, and VivoTag-5750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source). TABLE 1 lists a number of exemplary fluorochromes together with their spectral properties.

TABLE 1

| Fluorochrome | $\epsilon_{max}$ $M^{-1}cm^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFlour660 | 132,000 | 663 |
| AlexaFlour680 | 184,000 | 679 |
| AlexaFlour750 | 280,000 | 749 |
| VivoTag680 (VT680) | 100,000 | 670 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |

Alternatively, the near-infrared fluorochrome molecule is represented by Formula II or Formula III.

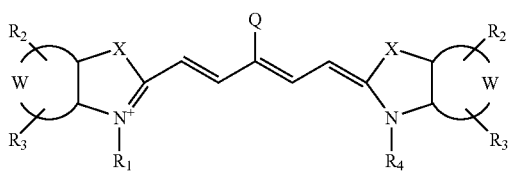

Formula II or a salt thereof, wherein:
X is independently selected from the group consisting of $C(CH_2Y_1)(CH_2Y_2)$, O, S, and Se;
$Y_1$ and $Y_2$ are independently selected from the group consisting of H, $C_1$-$C_{20}$ aliphatic group, and a $C_1$-$C_{20}$ aliphatic group substituted with —OR*, $N(R^*)_2$ or —SR*;
W represents a benzo-condensed, a naphtho-condensed or a pyrido-condensed ring;
$R_1$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6;
$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;
$R_4$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6; and
Q is selected from a group consisting of a heteroaryl ring substituted with a carboxyl group or 6-membered heteroaryl ring substituted with a carbonyl group.

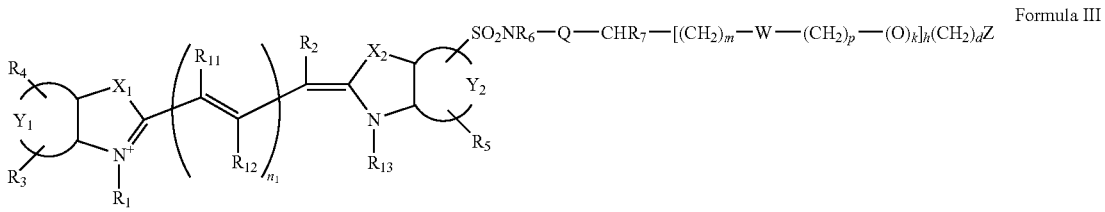

Formula III or a salt thereof, wherein:
$X_1$ and $X_2$ are independently selected from the group consisting of $C(CH_2K_1)(CH_2K_2)$, O, S and Se;
$K_1$ and $K_2$ are independently selected from the group consisting of H, a $C_1$-$C_{20}$ aliphatic group and a $C_1$-$C_{20}$ aliphatic group substituted with —OR*, $N(R^*)_2$ or —SR*; or $K_1$ and $K_2$ together are part of a substituted or unsubstituted carbocyclic or heterocyclic ring;
$Y_1$ and $Y_2$ are each independently a benzo-condensed ring, a naphtha-condensed ring or a pyrido-condensed ring;
$R_2$, $R_{11}$ and $R_{12}$ are independently H, halogen, alkyl, alkoxy, aryloxy, aryl, a sulfonate, a group containing $SO_2NR_6$-Q-$CHR_7$—$(CH_2)_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;
$R_1$ and $R_{13}$ are —H, $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;
$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, $N(R^*)_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or
$R_6$ is H, when Q is a carbonyl; and
$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, $N(R^*)_2$ or SR*; or
$R_6$ and $R_7$, taken together form a 4-, 5-, 6- or 7-membered heterocyclic or non-aromatic heterocyclic ring optionally substituted with halogen, OR*, $N(R^*)_2$ or SR*; or
$NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, $N(R^*)_2$ or —SR*; and W is absent or is a group selected from the group consisting of —SO$_2$NR$_6$-Q-CHR$_7$—, —O—, —COO—, and —CONH—;

Z is, or contains a N, O or S nucleophile functionality or is, or contains a functionality capable of reacting with N, O or S nucleophiles;

h=0-70;
k=0 or 1;
d=0-12;
m=0-12;
n$_1$ is 1, 2, or 3;
p=0-12; and
each R* is independently —H or C$_{1-20}$ alkyl.

Other useful near-infrared fluorochromes include, for example,

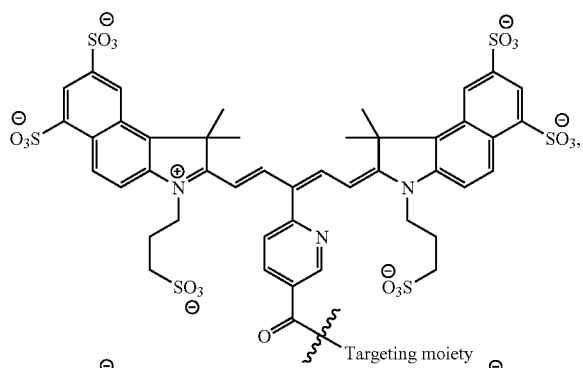

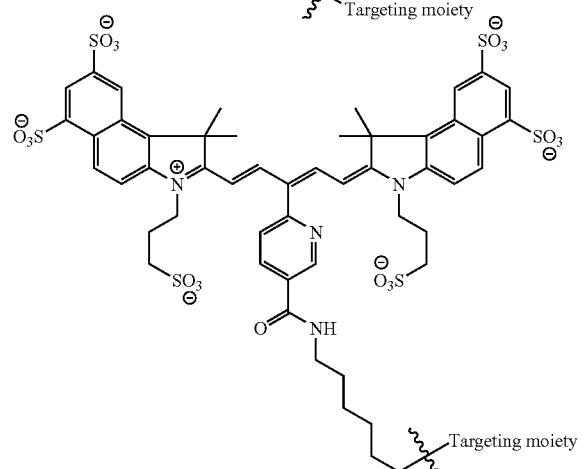

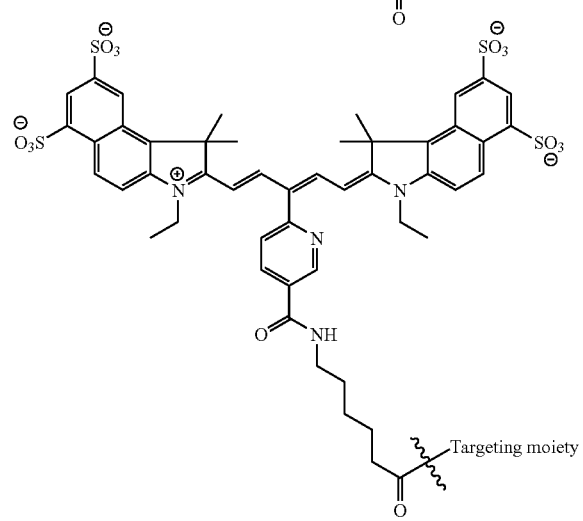

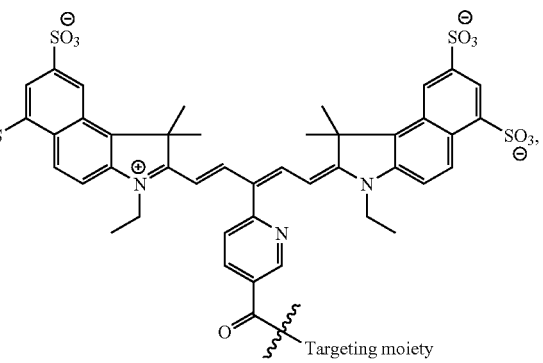

wherein the fluorochromes can be attached to the targeting moiety either directly (for example, via a chemical bond) or indirectly (for example, via a chemical linker or a carrier).

Other fluorochromes useful in the practice of the invention include, for example, fluorescein, rhodamine, texasRed, and BODIPY.

Alternatively, the fluorescence imaging moiety can be a fluorescent quantum dot, for example, amine T2MP EviTags (Evident Technologies) or Qdot Nanocrystals (Invitrogen). In general, fluorescent quantum dots are nanocrystals containing several atoms of a semiconductor material (containing cadmium and selenium or tellurium), which have been coated with zinc sulfide to improve the properties of these fluorescent agents.

Similarly, it is understood that the fluorescence imaging moiety can be a nanoparticle comprising silicon in a form that has fluorescent or luminescent properties. Aggregates of crystalline silicon (as multiple or single crystals of silicon), porous silicon, or amorphous silicon, or a combination of these forms, can form such nanoparticles. Preferred fluorescent silicon nanoparticles have a diameter between about 0.5 nm to about 25 nm, more preferably between about 2 nm and about 10 nm. The size of nanoparticles can be determined by laser light scattering or by atomic force microscopy or other suitable techniques.

Fluorescent silicon nanoparticles can have excitation and emission spectra 200 to 2000 nm, however, preferred fluorescent silicon nanoparticles have excitation and emission maximum between about 400 nm and about 1200 nm (and preferably 500 nm-900 nm, for example, 500 nm-600 nm, 600 nm-700 nm, 700 nm-800 nm, or 800 nm-900 nm). Preferred fluorescent silicon nanoparticles also have extinction coefficients of at least 50,000 M$^{-1}$cm$^{-1}$ in aqueous medium. Although fluorescent silicon nanoparticles that have excitation and emission maximum between 400 nm and 1200 nm are preferred, it will be appreciated that the use of fluorescent silicon nanoparticles with excitation and emission wavelengths in other spectrums can also be employed in the compositions and methods of the present invention. For example, in certain embodiments, the particles may have excitation approximately about 300-350 nm, and emission approximately about 400-450 nm.

Fluorescent silicon nanoparticles useful in the practice of the invention also have the following properties: (1) high quantum yield (i.e., quantum yield greater than 5% in aqueous medium), (2) narrow emission spectrum (i.e., less than 75 nm; more preferably less than 50 nm), (3) spectrally separated absorption and emission spectra (i.e., separated by more than 20 nm; more preferably by more than 50 nm), (3) have high chemical stability and photostability (i.e., retain luminescent properties after exposure to light), (4) are biocompatible or can be made more biocompatible; (5) are non toxic or minimally toxic to cells or subjects at doses used for imaging protocols, (as measured for example, by $LD_{50}$ or irritation studies, or other similar methods known in the art) and/or (6) have commercial viability and scalable production for large quantities (i.e., gram and kilogram quantities) required for in vivo and human use.

Furthermore, the fluorescence imaging moiety can be a fluorescent agent useful in photodynamic therapy, including, for example, Photofrin, Lutrin, Antrin, aminolevulinic acid, hypericin, benzoporphyrin derivative, and certain porphyrins.

C. Carriers

It is understood that the fluorescence imaging moieties can be attached to the targeting moiety either directly or indirectly, for example, via a linker or a carrier.

Exemplary carriers include, for example, polymers, for example, polymer backbones and particles. The design of the carrier will depend on considerations such as biocompatibility (e.g., toxicity and immunogenicity), serum half-life, useful functional groups (for conjugating fluorochromes, linkers, and protective groups), and cost.

Useful types of polymer backbones include polypeptides (polyamino acids), polyethyleneamines, polysaccharides, aminated polysaccharides, aminated oligosaccharides, polyamidoamines, polyacrylic acids and polyalcohols. In some embodiments the polymer backbone can consist of a polypeptide formed from L-amino acids, D-amino acids, or a combination thereof. Such a polypeptide can be, for example, a polypeptide identical or similar to a naturally occurring protein, such as, albumin, a homopolymer, such as, polylysine, or a copolymer such as a D-tyr-D-lys copolymer. When lysine residues are present in the polymer, the $\in$-amino groups on the side chains of the lysine residues can serve as convenient reactive groups for covalent linkage of fluorochromes and linker (see, U.S. Pat. No. 6,592,847). When the carrier is a polypeptide, the molecular weight of the probe can be from 2 kD to 1000 kD, more preferably, more preferably from 4 kD to 500 kD A carrier may be chosen or designed so as to have a suitably long in vivo persistence time (half-life). Alternatively, a rapidly-biodegradable backbone, for example, polylysine can be used in combination with covalently-linked protective chains. Examples of useful protective chains include polyethylene glycol (PEG), methoxypolyethylene glycol (MPEG), methoxypolypropylene glycol, polyethylene glycol-diacid, polyethylene glycol monoamine, MPEG monoamine, MPEG hydrazide, and MPEG imidazole. The protective chain can also be a block-copolymer of PEG and a different polymer such as a polypeptide, polysaccharide, polyamidoamine, polyethyleneamine or polynucleotide. Synthetic, biocompatible polymers are discussed generally in Holland et al. (1992) "Biodegradable Polymers," ADVANCES IN PHARMACEUTICAL SCIENCES 6:101-164.

A useful backbone-protective chain combination is methoxypoly(ethylene)glycol-succinyl-N-$\in$-poly-L-lysyine (PL-MPEG). The synthesis of this material, and other polylysine backbones with protective chains, is described in U.S. Pat. No. 5,593,658 and Bogdanov et al. (1995) ADVANCED DRUG DELIVERY REVIEWS 16:335-348.

Exemplary activatable probes employing a polymeric carrier are described, for example, in U.S. Pat. Nos. 6,083,486 and 6,592,847, which disclose intramolecularly-quenched near infrared fluorescence probes that emit substantial fluorescence only after activation, for example, after interaction with a molecular target. The probes comprise a polymeric backbone and a plurality of near infrared fluorochromes covalently linked to the backbone at fluorescence-quenching interaction-permissive positions separable, for example, by enzymatic cleavage at fluorescence activation sites. The fluorescence activation sites can be, for example, a substrate for an enzyme of interest. The term "fluorescence-quenching interaction-permissive positions" is understood to mean the positions of two or more atoms (in a single carrier) to which fluorochromes can be covalently linked (directly or through a linker) and maintained at fluorescence-quenching interaction-permissive positions relative to one another.

In certain embodiments, the probe comprises at least two fluorochromes (for example, two near-infrared fluorochromes, where one fluorochrome is capable or quenching the other, or one near-infrared fluorochrome and a quencher) attached to a fluorochrome attachment moiety at fluorescence-quenching interaction-permissive sites separated by a fluorescence activation site (e.g., a substrate for an enzyme). The imaging probe can be activatable by cleavage at the fluorescence activation site. Exemplary protease cleavage sites include a substrate for one or more enzymes selected from the group consisting of thrombin, fibrin, trypsin, plasmin, protein C, cathepsin, matrix metalloproteinase, a cysteine protease, a serine protease, an aspartic protease, and activator of factor Xa.

Alternatively, useful carriers include, for example, particles, for example, nanoparticles. A number of fluorescent agents can be covalently associated to the nanoparticles via chemical conjugation to reactive groups present in the nanoparticles or present in a coating disposed about the nanoparticles. The number of fluorescent moieties added per nanoparticle will vary depending upon the chemistries involved and the intended use of the nanoparticles.

In one embodiment, one or more fluorescent moieties are conjugated to metal oxide nanoparticles that have one or more of the following features: (1) a polymer coating suitable for attaching a plurality of fluorochromes thereby achieving large extinction coefficients (in excess of 1,000,000 $M^{-1}cm^{-1}$), (2) a non-crosslinked polymer coating suitable for attaching from about 10 to about 300 fluorochromes per particle, (3) a polymer coating suitable for attaching a plurality of fluorochromes in a manner that does not significantly compromise the quantum yield of the fluorochromes (e.g., the nanoparticles retain at least 50% of the fluorescent signal that is created by substantially the same number of free fluorochromes when tested under the same conditions), and (4) a polymer coating amenable to efficient chemical linking of biomolecules with retention of their biological properties to yield molecular imaging agents. The resulting fluorescent metal oxide nanoparticles are highly stable molecular imaging agents in vitro, both before and after chemical linking of fluorochromes and integrin agents, but yet are labile and/or degradable in vivo. Exemplary fluorescent nanoparticles and their synthesis are described in International Application Publication No. WO07/136,413.

It is understood that the chemistries used to conjugate the targeting moieties to the fluorochromes, either directly or indirectly, is known to those skilled in the art and so are not discussed in detail herein.

In certain embodiments, a probe with a targeting moiety and one or more fluorochromes can be used to image stent thrombosis. Exemplary probes for targeting thrombin include Gly-D-Phe-Pip(pipecolic acid)-Arg-Ser-Gly-Gly-Gly-Gly-Lys-Cys (SEQ ID NO.:25) covalently linked to Cy5.5 (as disclosed in Jaffer et al. (2002) ARTERIOSCLEROSIS THROMBOSIS VASCULAR BIOLOGY 22:1929-1935). Exemplary probes for targeting Factor XIIIa include Gly-Asn-Gln-Glu-Gln-Val-Ser- Pro-Leu-Thr-Leu-Leu-Lys-Trp-Cys (SEQ ID NO.:26) or Gly-Asn-Gln-Glu-Gln-Val-Ser-Pro-Leu-Thr-Leu-Leu-Lys-Cys (SEQ ID NO.:27) covalently linked to AlexaFluor 680 (as disclosed in Jaffer et al. (2004) CIRCULATION 110:170-176). Exemplary probes for targeting Factor XIII include Gly-Asn-Gln-Glu-Gln-Val-Ser-Pro-Leu-Thr-Leu-Leu-Lys-Trp-Cys (SEQ ID NO.:26) covalently linked to AlexaFluor 680; Gly-Asn-Ala-Glu-Gln-Val-Ser-Pro-Leu-Thr-Leu-Leu-Lys-Trp-Cys (SEQ ID NO.:28) covalently linked to AlexaFluor 680; and Gly-Asn-Gln-Glu-Gln-Val-Ser-Pro-Leu-Thr-Leu-Leu-Lys-Trp (SEQ ID NO.:29) covalently linked to gadolinium through a DOTA (1,4,7,10-tetraazacyclododecane-N,N',N'',N'''-tetraacetic acid) analogue (as disclosed in Tung et al. (2003) CHEMBIOCHEM 4:897-899). Exemplary probes for imaging cardiomyocyte apoptosis include annexin V covalently linked to the amino CLIO (cross-linked iron oxide) nanoparticle and Cy5.5 (as disclosed in Sosnovik et al. (2005) MAGNETIC RESONANCE IN MEDICINE 54:718-724). Exemplary probes for targeting integrins include a disulfide-linked cyclic RGD peptide (Gly-Gly-Gly-Cys-Arg-Gly-Asp-Cys (SEQ ID NO.:30) covalently linked to the amino CLIO (cross-linked iron oxide) nanoparticle and Cy5.5 or Cy3.5 (as disclosed in Montet et al. (2006) NEOPLASIA 8:214-222). Exemplary probes for targeting VCAM-1 include Val-His-Pro-Lys-Gln-His-Arg (SEQ ID NO.:12), Thr-Ala-Ser-Asn-Asn-Asn-Ser (SEQ ID NO.:31), Thr-Ile-Ser-Asn-Lys-Ser-Gln (SEQ ID NO.:32), Thr-Tyr-Ser-Asn-Ser-Tyr-Pro (SEQ ID NO.:33), Val-His-Ser-Pro-Asn-Lys-Lys (SEQ ID NO.:13), Arg-Gln-Pro-Leu-Pro-Thr-Gln (SEQ ID NO.:34), Pro-Leu-Pro-Thr-Gln-Val-Arg (SEQ ID NO.:35), or Asn-Ile-Arg-Pro-Leu-Pro-Met (SEQ ID NO.:36) covalently linked to Cy5.5 (as disclosed in Nahrendorf et al. (2006) CIRCULATION 114:1504-1511). Exemplary probes for targeting fibrin include Gly-Pro-Arg-Pro-Pro-Lys (SEQ ID NO.:7) covalently linked to a fluorophore such as Cy5.5 (as disclosed in Aruva et al. (2006) J. NUCLEAR MEDICINE 47:155-162) and Gly-Pro-Arg-Pro-Pro-Gly-Gly-Ser-Lys-Gly-Cys (SEQ ID NO.:37) covalently linked to both a near-infrared fluorochrome, for example, Cy5.5 or VT 680 and a CLIO particle (as disclosed in McCarthy et al. (2009) BIOCONJUGATE CHEM. 20:1251-1255). An exemplary probe for targeting Factor XIII includes Gly-Asn-Gln-Glu-Gln-Val-Ser-Pro-Leu-Thr-Leu-Leu-Lys-Cys (SEQ ID NO.:27) covalently linked to both a fluorophore such as VT 680 and a CLIO particle (as disclosed in McCarthy et al. (2009) supra).

In certain embodiments, exemplary probes for targeting fibrin include as targeting moieties the linear peptides WQPCPAESWTFCWDPGSAGSK (SEQ ID NO.:38) and WQPCPAESWTFCWDPGAGSGK (SEQ ID NO.:39) as well as the cyclic peptides GWQPC*PWESWTFC*WDP (SEQ ID NO.:40); SGSGJWQPC*PWESWTFC*WDP (SEQ ID NO.:41); RWQPC*PAESWT-Cha-C*WDP (SEQ ID NO.:42); RWQPC*PWESWTFC*WDP (SEQ ID NO.:43); WQPC*PAESWTFC*WDP (SEQ ID NO.:44); SGSGSGSGWQPC*WESWTFC*WDP (SEQ ID NO.:45); RWQPC*PAESWTChaC*WDP (SEQ ID NO.:46); and WQPC*PAESWTFC*WDP (SEQ ID NO.:47); wherein the cysteines denoted with a "*" are linked by a disulfide bond and Cha represents cyclohexylalanine.

The formula for certain exemplary probes is represented by:

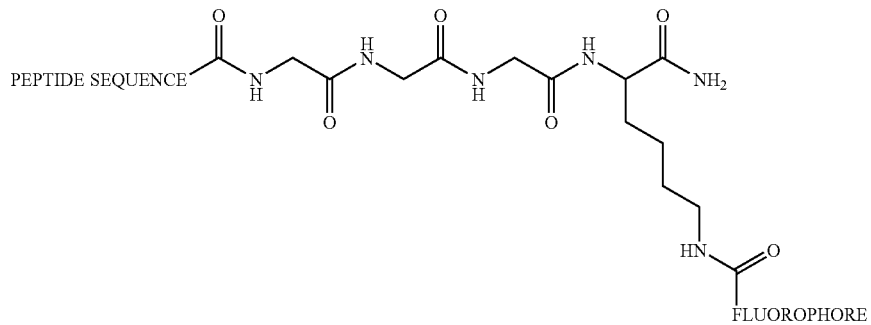

wherein the peptide sequence comprises one of the foregoing peptides. Alternatively, the formula may be represented by

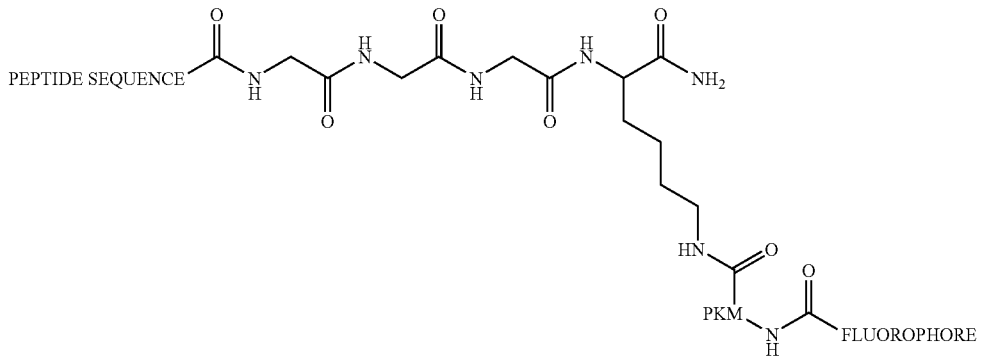

wherein the peptide sequence comprises one of the foregoing peptides and PKM is a pharmacokinetic modifier, which can include, for example, a polymer carrier discussed hereinabove in Section C.

Exemplary probes include, for example:

19
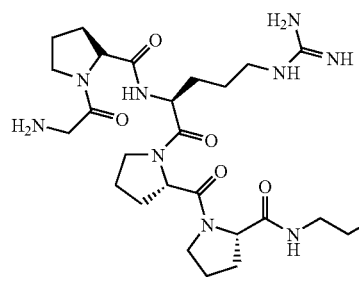
20
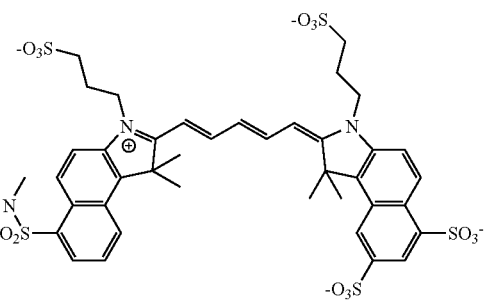
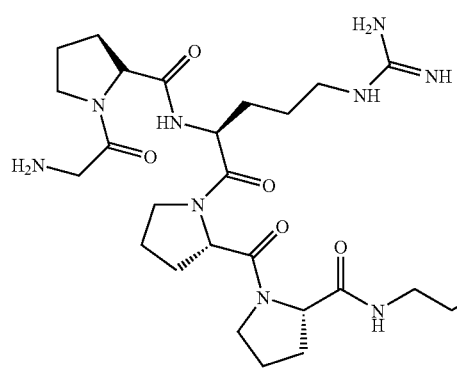
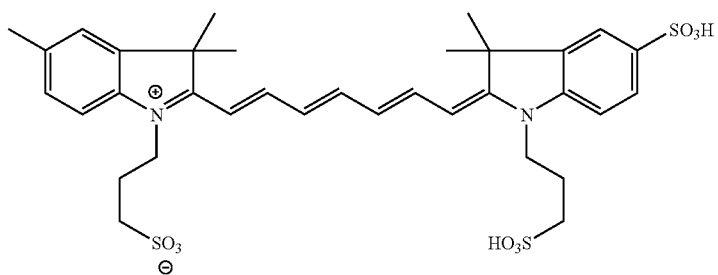
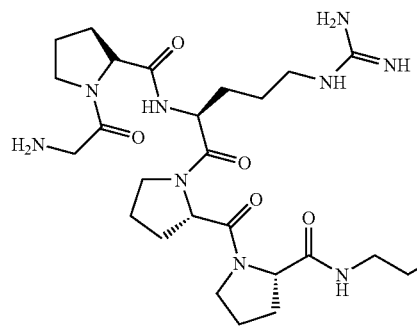
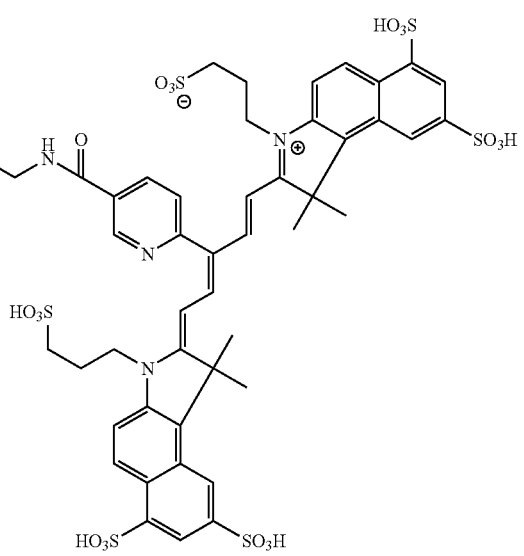

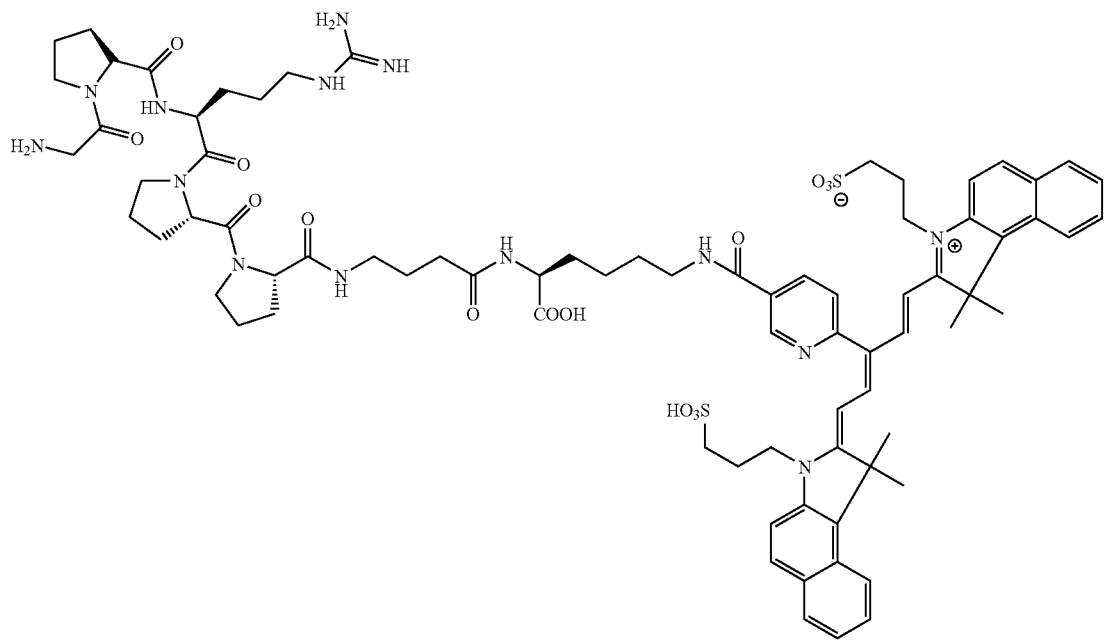
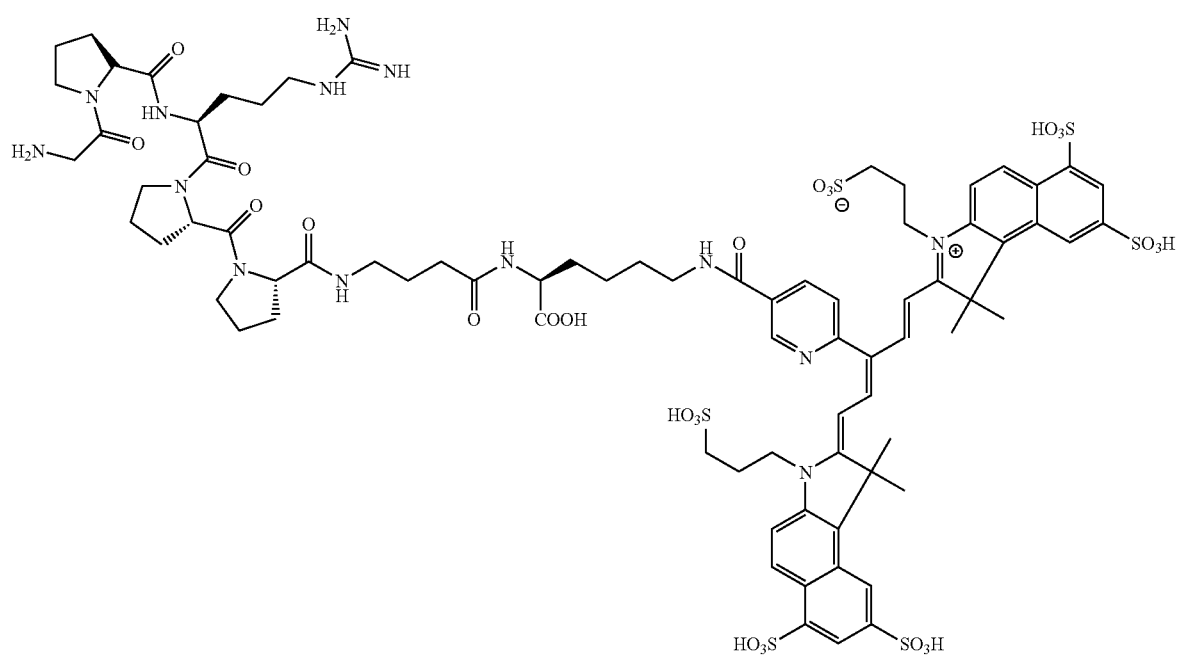

-continued
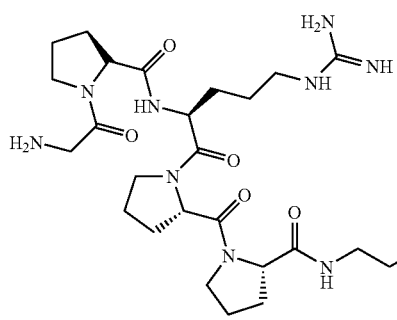
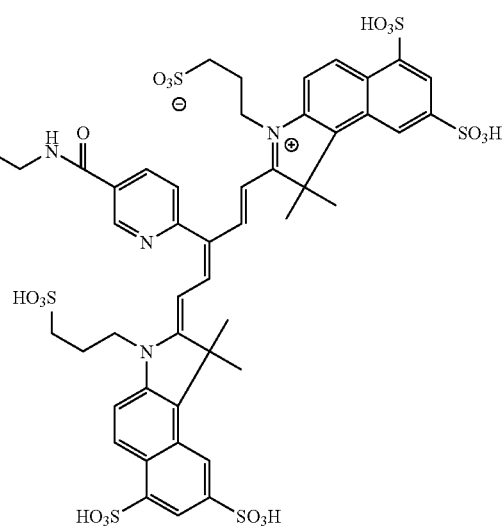
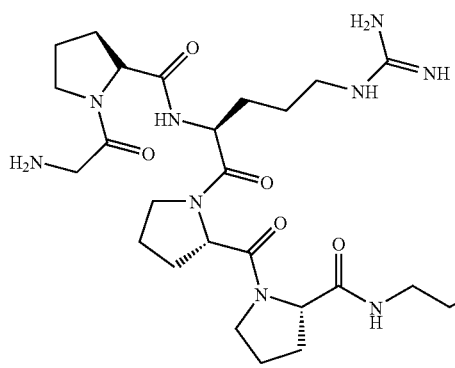
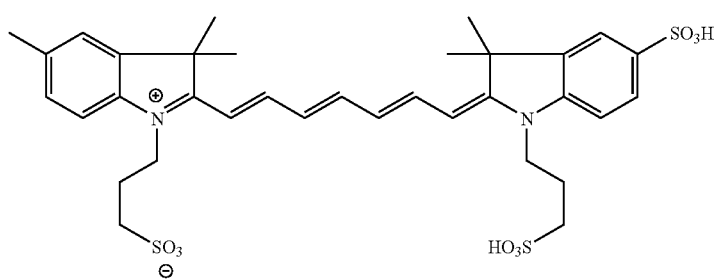
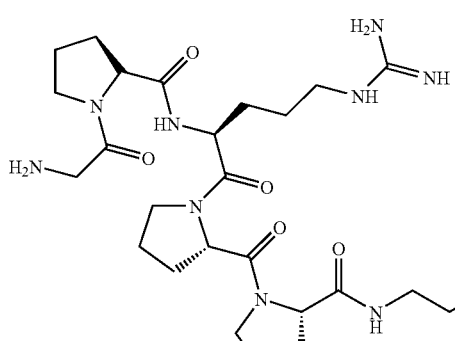
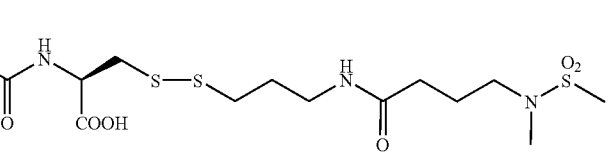

-continued

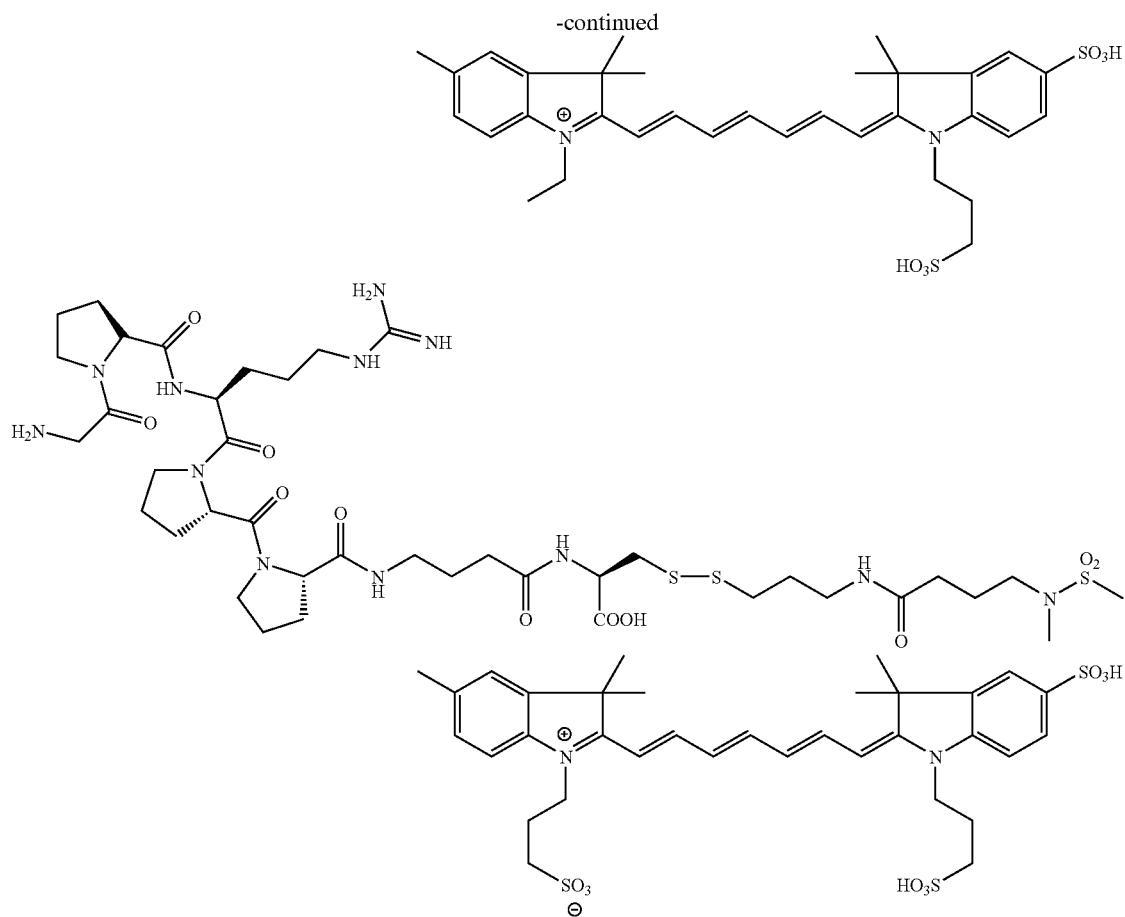

The invention also provides a stent capable of being imaged in vivo. The stent comprises (a) a stent dimensioned for implantation within a blood vessel; (b) a coating covering at least a portion of the stent; and (c) an activatable or targeted imaging probe associated with the coating or an exposed metallic surface of the stent. The coating can include, for example, fluorescently labeled quenched substrates of enzymes implicated in thrombus formation at a stent. Exemplary enzymes include, for example, activated Factor XII, activated Factor XI, activated Factor IX, activated Factor VIII, activated Factor Xa, activated Factor V, thrombin, activated Factor XIII, and activated Factor VII.

Exemplary coatings include, for example, polyethylene-co-vinyl acetate, poly n-butyl methacrylate, poly(styrene-b-isobutylene-b-styrene), phosphorylcholine, fluorinated co-polymer, silicon carbide, gold, titanium nitride oxide, and carbon.

The activatable imaging probe comprises a fluorochrome attachment moiety and a plurality of near-infrared fluorochromes linked to the fluorochrome attachment moiety at fluorescence-quenching interaction-permissive positions. The fluorescence-quenching interaction-permissive positions are separated by a fluorescence activation site (for example, a protease cleavage site), wherein in the intact probe a first near-infrared fluorochrome quenches a second near-infrared fluorochrome. The probe is activatable by cleavage at the fluorescence activation site whereupon the first fluorochrome no longer quenches the second fluorochrome. Depending upon the choice of the fluorescence activation site, the probe may be activated when exposed to molecular markers indicative of stent thrombosis. As a result, the implanted stents cannot be visualized by fluorescence imaging until the surrounding environment activates the probe.

II. Administration of the Probes

For in vivo use, the probes generally are provided in a formulation suitable for administration to a subject. Accordingly, the formulations generally include the one or more probes together with a physiologically relevant carrier suitable for the desired form and/or dose of administration. The term, "physiologically relevant carrier" is understood to mean a carrier in which the agents are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

It is contemplated that the probes can be administered orally or parenterally or be locally adherent to the stent at the time of stent implantation. For parenteral administration, the agents can be administered, by conventional routes, including for example, intravenously, intramuscularly, cutaneously, percutaneously, subcutaneously, rectally, nasally, and vaginally.

Depending upon the mode of administration, the composition containing the probe may be in the form of, for example, solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The probes compositions can be formulated according to conventional pharmaceutical practice (see, e.g., REMINGTON: THE SCIENCE AND PRACTICE OF PHARMACY, 20th edition, 2000, ed. A. R. Germaro, Lippincott Williams & Wilkins, Philadelphia, and ENCYCLOPEDIA OF PHARMACEUTICAL TECHNOLOGY, eds. J. Swarbrick and J. C. Boylan, 1988-1999, Marcel Dekker, New York).

The amount of probe to be administered is determined using techniques known to those skilled in the art, and will vary depending up, for example, the brightness (extinction coefficient) of a particular probe, the mode of imaging, the sensitivity of the detection system, and the age, weight, and health of the subject being imaged.

III. Imaging System Considerations

An imaging system useful in the practice of this invention typically includes three basic components: (1) an appropriate light source for exciting the fluorescence moiety present in the probe, (2) a system for separating or distinguishing emissions from light used for inducing excitation of the fluorescence moiety, and (3) a detection system. The detection system can be hand-held or incorporated into other useful imaging devices such as endoscopes, catheters, intraoperative microscopes and/or viewers.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al (1994) PROC. NATL. ACAD. SCI. USA 91:4887-4891; Ntziachristos et al. (2000) PROC. NATL. ACAD. SCI. USA 97:2767-2772; and Alexander (1991) J. CLIN. LASER MED. SURG. 9:416-418. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al. (1999) J. PHOTOCHEM. PHOTOBIOL. B 52:131-135), ovarian cancer (Major et al. (1997) GYNECOL. ONCOL. 66:122-132), colon and rectum (Mycek et al. (1998) GASTROINTEST. ENDOSC. 48:390-394; and Stepp et al. (1998) ENDOSCOPY 30:379-386), bile ducts (Izuishi et al. (1999) HEPATOGASTROENTEROLOGY 46:804-807), stomach (Abe et al. (2000) ENDOSCOPY 32:281-286), bladder (Kriegmair et al. (1999) UROL. INT. 63:27-31; and Riedl et al. (1999) J. ENDOUROL. 13:755-759), lung (Hirsch et al. (2001) CLIN. CANCER RES. 7:5-220), brain (Ward, J. (1998) LASER APPS. 10:224-228), esophagus, and head and neck regions can be employed in the practice of the present invention.

Other types of light gathering components are catheter-based devices, including fiber optics devices. Such devices are particularly suitable for intravascular imaging. See, for example, Tearney et al. (1997) SCIENCE 276:2037-2039; Tearney et al. (1996) CIRCULATION 94:3013; Zhu et al. (2005) J. PHYS. D.: APPLIED PHYSICS 38:2701-2707; Jaffer et al. (2008) CIRCULATION 118:1802-1809.

Still other imaging technologies, including phased array technology (Boas et al. (1994) supra; Chance (1998) ANN. NY ACAD. SCI. 838:29-45), optical tomography (Cheng et al. (1998) OPTICS EXPRESS 3:118-123; and Siegel et al. (1999) OPTICS EXPRESS 4:287-298), intravital microscopy (Dellian et al. (2000) BR. J. CANCER 82:1513-1518; Monsky et al. (1999) CANCER RES. 59:4129-4135; and Fukumura et al. (1998) CELL 94:715-725), confocal imaging (Korlach et al. (1999) PROC. NATL. ACAD. SCI. USA 96:8461-8466; Rajadhyaksha et al. (1995) J. INVEST. DERMATOL. 104:946-952; and Gonzalez et al. (1999) J. MED. 30:337-356) and fluorescence molecular tomography (FMT) (Nziachristos et al. (2002) NATURE MEDICINE 8:757-760; U.S. Pat. No. 6,615,063, International Application Publication No. WO 03/102558, and International Application Serial No. PCT/US03/07579) can be used with the fluorochrome compounds of the invention.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

Optical imaging devices and measurement techniques include, but are not limited to, fluorescence imaging, luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography.

Commercially available systems include but are not limited to, eXplore Optix and SoftScan (ART—Advanced Research Technologies), NightOWL II LB (Berthold Technologies), NanoSPECT and HiSPECT (Bioscan), Maestro FLEX and Nuance FLEX (Cambridge Research and Instrumentation—CRi), LightSpeed, BrightSpeed and MR Signa Series (GE Healthcare), Kodak In-Vivo Imaging FX Systems and Kodak Image Station 4000 series (KODAK and Carestream), Aquacosmos (Hamamatsu), CTLM and LILA Imaging Systems (Imaging Diagnostic Systems—IMDS), Odyssey Infrared Imaging System (LI-COR), IMRIS Neuro System (IMRIS), SPY and SPY-TMR Systems, HELIOS, LUNA, and OPTTX Imaging Systems (Novadaq), DYNOT Imaging System (NIRx), and IVIS Systems, IVIS Spectrum and IVIS Lumina (Xenogen and Caliper Life Sciences).

The systems can include a computer that executes software that controls the operation of one or more instruments, and/or that processes data obtained by the system. The software can include one or more modules recorded on machine-readable media, such as, magnetic disks, magnetic tape, CD-ROM, and semiconductor memory. The machine-readable medium can be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term, "machine-readable instructions," as used herein is intended to encompass software, hardwired logic, firmware, object code and the like.

The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

An exemplary catheter based system useful in the practice of the invention is described as follows. For example, the source of excitation light is a continuous-wave laser diode with an excitation wavelength of 750 nm (B&W TEK, Newark, Del.). The excitation light then is filtered with a narrow-bandpass interference filter centered at 752 nm and with a 5 nm full width at half-maximum to remove residual laser scatter. The filtered excitation light is guided with a multimode fiber after passing through a 3-dB beam splitter and coupled into a dedicated catheter prototype based on an optical coherence tomography wire (LightLab Imaging Inc, Westford, Mass.). The catheter can contain a 0.36-mm/0.014-in floppy radiopaque tip with a 0.41-mm/0.016-in OD housing a 62.5/125 micron multimode fiber 200 cm long. A prism located at the end of the catheter can direct the light at 90° with respect to the catheter, which is then focused on a near diffraction-limited focal spot size of approximately 40 microns. Emitted fluorescent light then is collected back into the catheter and guided to the beam splitter, where one half of the photon flux is coupled into a separate multimode fiber. In order to limit contamination by backscattered light, fluorescence photons can be filtered with a dielectrically coated dichroic filter with a cut-on wavelength of 780 nm. The residual fluorescence light then is detected with a photomultiplier tube (H5783-20, Hamamatsu, Shizuoka, Japan) and digitized with 16-bit resolution at 1 kHz (DAQ card, National Instruments, Austin, Tex.) operating on a personal computer. Data noise reduction can be performed with a 50-point moving average filter (MatLab version 7.5, MathWorks, Natick, Mass.).

IV. Imaging Protocol, Data Collection and Analysis

During practice of the imaging method, the probe is administered to the subject using one of the administration routes described hereinabove. The probe then is given sufficient time, for example, from about 5 minutes to about 1500 minutes after administration to traverse and accumulate at the site of the stent. Thereafter, the excitation light is directed into the subject so as to excite a probe present in the vicinity of the stent. The fluorescent light emitted by the probe is captured by a detector. The resulting data can be used to determine whether one or more probes have accumulated at the site of the stent. Accumulation of one or more probes at the site of the stent is indicative that the subject, even in the absence of clinical manifestations, is at risk of developing stent thrombosis.

It is understood that, when using near-infrared fluorochromes, the fluorescence emission and detection can occur even in the presence of blood in the blood vessel being analyzed. In other words, such a process is minimally invasive as the blood flow past the stent being interrogated is not interrupted. It is understood, however, that under certain circumstances, it may be advantageous not to have blood present in the blood vessel at the time of imaging. This can be achieved by transient saline flushing through a vessel guiding catheter, and/or proximal balloon occlusion with or without saline perfusion through the balloon.

The invention will now be illustrated by means of the following example which is given for the purpose of illustration only and without any intention to limit the scope of the present invention.

EXAMPLES

Example 1

Imaging of Stent Thrombosis

This example describes a method of imaging a stent in an animal model.

A coronary stent (2.5-3.5 mm) is implanted into the iliac artery of a rabbit (with or without atheroma), or coronary artery of a pig. Stents will either be drug eluting or bare metal. At time points between 1 and 180 days post implantation, a fluorescence imaging agent comprising Prosense750 (80 nmol/kg) or CLIO-VT680 (10 mg Fe/kg) or GPRPPK (SEQ ID NO.:7) covalently attached to Cy5.5 at a concentration of 2 nM is administered intravenously in a 200 microliter bolus. After a time to allow targeting/activation, a catheter, angioscope, or other fluorescence imaging system is inserted intravascularly adjacent to the stent. Pullbacks will be obtained to detect fluorescence, with and without the presence of blood. Co-registration with other imaging modalities (e.g. intravascular ultrasound (IVUS) or optical coherence tomography/optical frequency domain imaging), can also be performed. Animals are then sacrificed. Fluorescence reflectance imaging and confocal microscopy will be performed. Stents are then processed for histopathology and sectioning to confirm the presence of the molecular marker.

Incorporation By Reference

The entire disclosure of each of the patent and scientific documents referred to herein is incorporated by reference for all purposes.

Equivalents

Although the present invention has been illustrated by means of preferred embodiments thereof, it is understood that the invention intends to cover broad aspects thereof without departing from the spirit and scope of the invention as defined in the appended claims.

What is claimed is:

1. A stent capable of being imaged in vivo during asymptomatic stent thrombosis comprising:
   (a) a stent dimensioned for implantation within a blood vessel; and
   (b) a stent coating covering at least a portion of the stent and comprising
   an imaging probe activatable during asymptomatic stent thrombosis, wherein the activatable imaging probe comprises a fluorochrome attachment moiety and a plurality of near-infrared fluorochromes linked to the fluorochrome attachment moiety at fluorescence-quenching interaction-permissive positions separated by a fluorescence activation site selectively cleavable by activated Factor XII, activated Factor XI, activated Factor IX, activated Factor VIII, activated Factor Xa, activated Factor V, thrombin, activated Factor XIII, or activated Factor VII; wherein a first near-infrared fluorochrome quenches a second near-infrared fluorochrome and the probe is activatable by cleavage at the fluorescence activation site whereupon the first fluorochrome no longer quenches the second fluorochrome and the fluorochromes become detectable during asymptomatic stent thrombosis.

2. The stent of claim 1, wherein the first and second near-infrared fluorochromes are different.

3. The stent of claim 1, wherein at least one of the fluorochromes is selected from the group consisting of a carbocyanine dye and an indocarbocyanine fluorochrome.

4. The stent of claim 1, wherein at least one of the near-infrared fluorochromes is selected from the group consisting of Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, and DyLight647, HiLyte Fluor 680, HiLyte Fluor 750, IRDye800CW, IRDye 800RS, IRDDye 700DX, ADS780WS, and ADS832WS.

5. The stent of claim 1, wherein at least one of the near-infrared fluorochrome molecules is represented by Formula II:

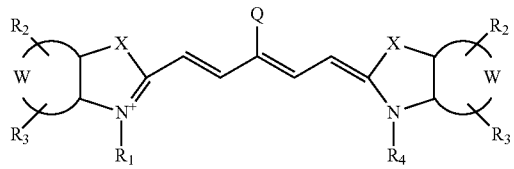

or a salt thereof, wherein:
X is independently selected from the group consisting of $C(CH_2Y_1)(CH_2Y_2)$, O, S, and Se;
$Y_1$ and $Y_2$ are independently selected from the group consisting of H, $C_1$-$C_{20}$ aliphatic group, and a $C_1$-$C_{20}$ aliphatic group substituted with —OR*, N(R*)$_2$ or —SR*;
W represents a benzo-condensed, a naphtho-condensed or a pyrido-condensed ring;
$R_1$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6;
$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;
$R_4$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6; and
Q is selected from a group consisting of a heteroaryl ring substituted with a carboxyl group or 6-membered heteroaryl ring substituted with a carbonyl group.

6. The stent of claim 1, wherein at least one of the near-infrared fluorochrome molecules is represented by Formula III:

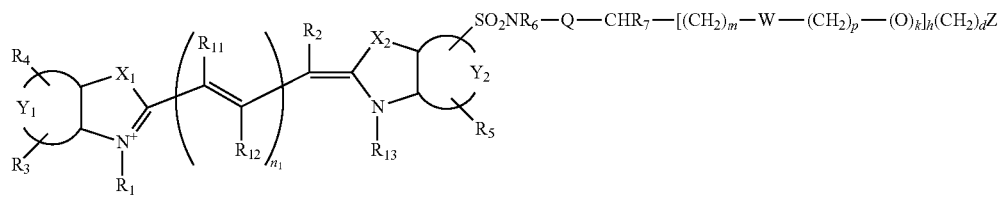

or a salt thereof, wherein:
$X_1$ and $X_2$ are independently selected from the group consisting of $C(CH_2K_1)(CH_2K_2)$, O, S and Se;
$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic or heterocyclic ring;
$Y_1$ and $Y_2$ are each independently a benzo-condensed ring, a naphtha-condensed ring or a pyrido-condensed ring;
$R_2$, $R_{11}$ and $R_{12}$ are independently H, halogen, alkyl, alkoxy, aryloxy, aryl, a sulfonate, a group containing $SO_2NR_6$-Q-$CHR_7$-$(CH_2)_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;
$R_1$ and $R_{13}$ are —H, $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;
$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_7$-$C_6$ carbocyclic, non-aromatic carbocyclic, heterocyclic or non-aromatic heterocyclic ring wherein the heterocyclic rings contains 1-2 heteroatoms; or
$R_6$ is H, when Q is a carbonyl; and
$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or
$R_6$ and $R_7$, taken together form a 4-, 5-, 6- or 7-membered heterocyclic or non-aromatic heterocyclic ring optionally substituted with halogen, OR*, N(R*)$_2$ or SR*; or
$NR_6$, Q and $CHR_7$ together form a substituted or unsubstituted heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of $-SO_2NR_6$-Q-$CHR_7-$, $-O-$, $-COO-$, and $-CONH-$;

Z is, or contains a N, O or S nucleophile functionality or is, or contains a functionality capable of reacting with N, O or S nucleophiles;

h=0-70;

k=0 or 1;

d=0-12;

m=0-12;

$n_1$ is 1, 2, or 3;

p=0-12; and each R* is independently $-H$ or $C_{1-20}$ alkyl.

* * * * *